US009039644B2

(12) United States Patent
Ingimundarson et al.

(10) Patent No.: US 9,039,644 B2
(45) Date of Patent: *May 26, 2015

(54) ORTHOPEDIC COMPONENT FOR USE WITH AN ORTHOPEDIC BRACE

(71) Applicant: Össur hf, Reykjavik (IS)

(72) Inventors: Arni Thor Ingimundarson, Gardabaer (IS); Palmi Einarsson, Kopavogur (IS)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,314

(22) Filed: Dec. 21, 2012

(65) Prior Publication Data

US 2013/0116610 A1  May 9, 2013

Related U.S. Application Data

(63) Continuation of application No. 12/068,782, filed on Feb. 12, 2008, now Pat. No. 8,348,876.

(60) Provisional application No. 60/900,719, filed on Feb. 12, 2007.

(51) Int. Cl.
*A61F 5/00* (2006.01)
*A41D 13/00* (2006.01)
(Continued)

(52) U.S. Cl.
CPC ............... *A61F 5/0123* (2013.01); *Y10T 24/21* (2015.01); *A61F 2005/0181* (2013.01); *A61F 5/01* (2013.01); *A41D 13/065* (2013.01)

(58) Field of Classification Search
CPC ....................................................... A61F 5/01
USPC ........ 602/26, 23, 5, 1, 16; 2/455, 22, 24, 255, 2/256, 257, 243.1, 258, 259, 263; 24/68 R, 69 SK, 69 TM, 68 SK, 68 D, 24/307, 308, 572.1, 573.09, 579.09, 24/579.11; 128/882
See application file for complete search history.

(56) References Cited

U.S. PATENT DOCUMENTS 1,390,915 A  9/1921  Loth
2,531,486 A  11/1950  Weber
(Continued)

FOREIGN PATENT DOCUMENTS

GB    2409625 A    7/2005
WO    2006/055620 A2    5/2006

OTHER PUBLICATIONS

Extended European Search Report from corresponding EP Application 08725444.7, Oct. 30, 2013.
(Continued)

*Primary Examiner* — Alireza Nia
*Assistant Examiner* — Tarla Patel
(74) *Attorney, Agent, or Firm* — Workman Nydegger

(57) ABSTRACT

An orthopedic component for use in orthopedic device includes a rigid frame and a flexible subshell connected to and extending flexibly outwardly from the rigid frame. The subshell may have a shell body and a perimeter edge portion defining a lip extending outwardly from a surface of a shell body and defining a clearance between the shell body and the lip. The subshell may include a plurality of slots and ventilated padding is used in combination with the slots. A tightenable fastener may be adjustably secured to the rigid frame and extend through an opening on the subshell, wherein the first side portion of the subshell is adjustable in location relative to the rigid frame.

13 Claims, 15 Drawing Sheets

(51) Int. Cl.
  *A43C 11/00* (2006.01)
  *A61F 5/01* (2006.01)
  *A41D 13/06* (2006.01)

(56) References Cited

U.S. PATENT DOCUMENTS

| | | | |
|---|---|---|---|
| 2,883,982 A | 4/1959 | Rainey |
| 3,030,634 A | 4/1962 | Bair |
| 3,099,448 A | 7/1963 | Salvo et al. |
| 3,259,910 A | 7/1966 | Daignault |
| 3,387,305 A | 6/1968 | Shafer |
| 3,669,105 A | 6/1972 | Castiglia |
| 3,779,654 A | 12/1973 | Horne |
| 3,785,372 A | 1/1974 | Craig |
| 3,817,244 A | 6/1974 | Taylor |
| 3,900,898 A | 8/1975 | Ackerman |
| 3,902,482 A | 9/1975 | Taylor |
| 3,928,872 A | 12/1975 | Johnson |
| 3,958,569 A | 5/1976 | Vosburgh |
| 4,068,312 A | 1/1978 | Ledsma |
| 4,136,404 A | 1/1979 | Lange |
| 4,169,467 A | 10/1979 | Rabischong et al. |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Erichsen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,490,855 A | 1/1985 | Figgie, III et al. |
| 4,493,316 A | 1/1985 | Reed et al. |
| 4,494,534 A | 1/1985 | Hutson |
| 4,503,846 A | 3/1985 | Martin |
| 4,523,585 A | 6/1985 | Lamb et al. |
| 4,554,913 A | 11/1985 | Womack et al. |
| D284,702 S | 7/1986 | Castillo |
| 4,599,748 A | 7/1986 | Garcia |
| 4,599,998 A | 7/1986 | Castillo |
| 4,603,690 A | 8/1986 | Skeen |
| 4,614,181 A | 9/1986 | Karlsson |
| 4,620,532 A | 11/1986 | Houswerth |
| 4,621,624 A | 11/1986 | Rayboy |
| 4,628,916 A | 12/1986 | Lerman et al. |
| 4,665,905 A | 5/1987 | Brown |
| 4,681,097 A | 7/1987 | Pansiera |
| 4,697,583 A | 10/1987 | Mason et al. |
| 4,699,129 A | 10/1987 | Aaserude et al. |
| 4,715,363 A | 12/1987 | Detty |
| 4,723,539 A | 2/1988 | Townsend |
| 4,753,240 A | 6/1988 | Sparks |
| D298,568 S | 11/1988 | Womack et al. |
| 4,791,916 A | 12/1988 | Paez |
| 4,803,975 A | 2/1989 | Meyers |
| 4,854,308 A | 8/1989 | Drillio |
| 4,856,501 A | 8/1989 | Castillo et al. |
| 4,886,054 A | 12/1989 | Castillo et al. |
| 4,938,207 A | 7/1990 | Vargo |
| 4,940,044 A | 7/1990 | Castillo |
| 4,964,402 A | 10/1990 | Grim et al. |
| 4,986,264 A | 1/1991 | Miller |
| 5,005,565 A | 4/1991 | Fratesi |
| D318,736 S | 7/1991 | Castillo |
| 5,063,916 A | 11/1991 | France et al. |
| 5,072,970 A | 12/1991 | Dandy, III et al. |
| 5,107,823 A | 4/1992 | Fratesi |
| 5,121,742 A | 6/1992 | Engen |
| 5,131,684 A | 7/1992 | Dandy, III et al. |
| 5,131,685 A | 7/1992 | Dandy, III et al. |
| 5,135,469 A | 8/1992 | Castillo |
| 5,230,697 A | 7/1993 | Castillo et al. |
| 5,288,287 A | 2/1994 | Castillo et al. |
| D346,028 S | 4/1994 | Lengyel |
| 5,334,135 A | 8/1994 | Grim et al. |
| D357,070 S | 4/1995 | Castillo |
| 5,445,602 A | 8/1995 | Grim et al. |
| 5,641,322 A | 6/1997 | Silver et al. |
| 5,695,452 A | 12/1997 | Grim et al. |
| 5,713,837 A | 2/1998 | Grim et al. |
| 5,716,335 A | 2/1998 | Iglesias et al. |
| 5,792,084 A | 8/1998 | Wilson et al. |
| 5,794,261 A | 8/1998 | Hefling |
| 5,807,294 A | 9/1998 | Cawley et al. |
| 5,823,931 A | 10/1998 | Gilmour |
| 5,865,777 A | 2/1999 | Detty |
| 5,951,504 A | 9/1999 | Iglesias et al. |
| 6,024,712 A | 2/2000 | Iglesias et al. |
| D433,756 S | 11/2000 | Castillo |
| 6,205,583 B1 | 3/2001 | Beland |
| D451,644 S | 12/2001 | Fujimoto et al. |
| 6,393,610 B1 | 5/2002 | Parks |
| 6,402,711 B1 | 6/2002 | Nauert |
| D463,886 S | 10/2002 | Cantu, Jr. |
| 6,540,709 B1 | 4/2003 | Smits |
| 6,689,080 B2 | 2/2004 | Castillo |
| 6,793,641 B2 | 9/2004 | Freeman et al. |
| 6,796,951 B2 | 9/2004 | Freeman et al. |
| D501,690 S | 2/2005 | Chen |
| 6,875,187 B2 | 4/2005 | Castillo |
| D504,981 S | 5/2005 | Vanderhoef |
| 6,932,780 B2 * | 8/2005 | Kozersky ............... 602/19 |
| 6,988,999 B1 | 1/2006 | Lin |
| D517,248 S | 3/2006 | Castillo et al. |
| 7,311,686 B1 | 12/2007 | Iglesias et al. |
| 7,941,867 B2 | 5/2011 | Olson |
| 8,048,013 B2 * | 11/2011 | Ingimundarson et al. ...... 602/26 |
| 8,151,369 B2 | 4/2012 | Olson |
| 2002/0107462 A1 | 8/2002 | Freeman et al. |
| 2002/0107464 A1 | 8/2002 | Castillo |
| 2002/0183674 A1 | 12/2002 | Castillo |
| 2004/0019949 A1 | 2/2004 | Crockett |
| 2005/0165338 A1 | 7/2005 | Iglesias et al. |
| 2005/0171461 A1 * | 8/2005 | Pick ............................ 602/27 |
| 2006/0100561 A1 | 5/2006 | Gilmour |
| 2006/0107433 A1 | 5/2006 | Olson |
| 2006/0135901 A1 | 6/2006 | Ingimundarson et al. |
| 2006/0135903 A1 | 6/2006 | Ingimundarson et al. |
| 2006/0167396 A1 | 7/2006 | Berger |
| 2007/0100266 A1 * | 5/2007 | Hargrave et al. ............ 602/21 |
| 2007/0225824 A1 | 9/2007 | Einarsson |
| 2007/0293798 A1 | 12/2007 | Hu et al. |
| 2011/0167546 A1 | 7/2011 | Olson |

OTHER PUBLICATIONS

Extended European Search Report from Corresponding EP Application 08725443.9, Dec. 10, 2013.

* cited by examiner

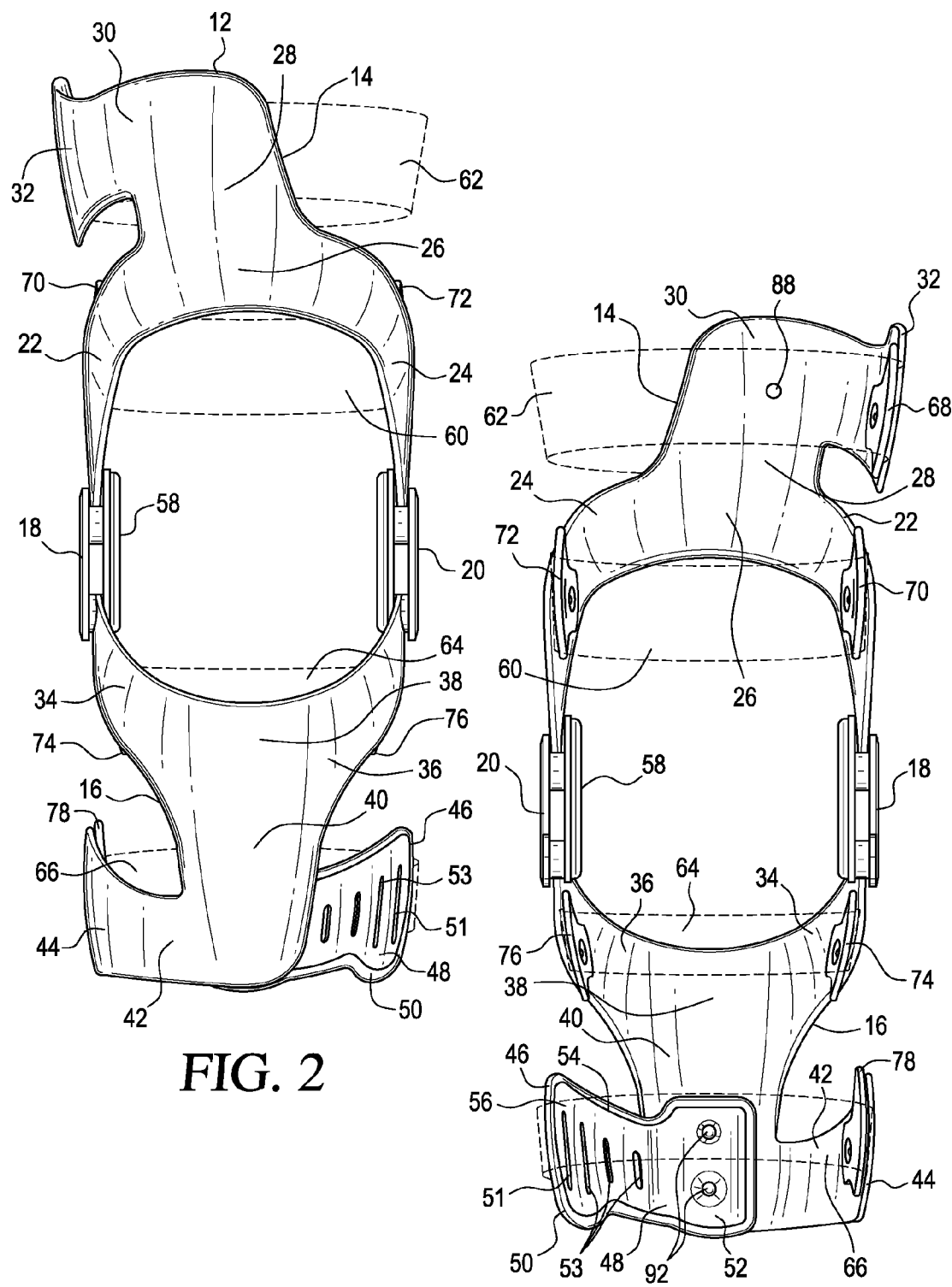

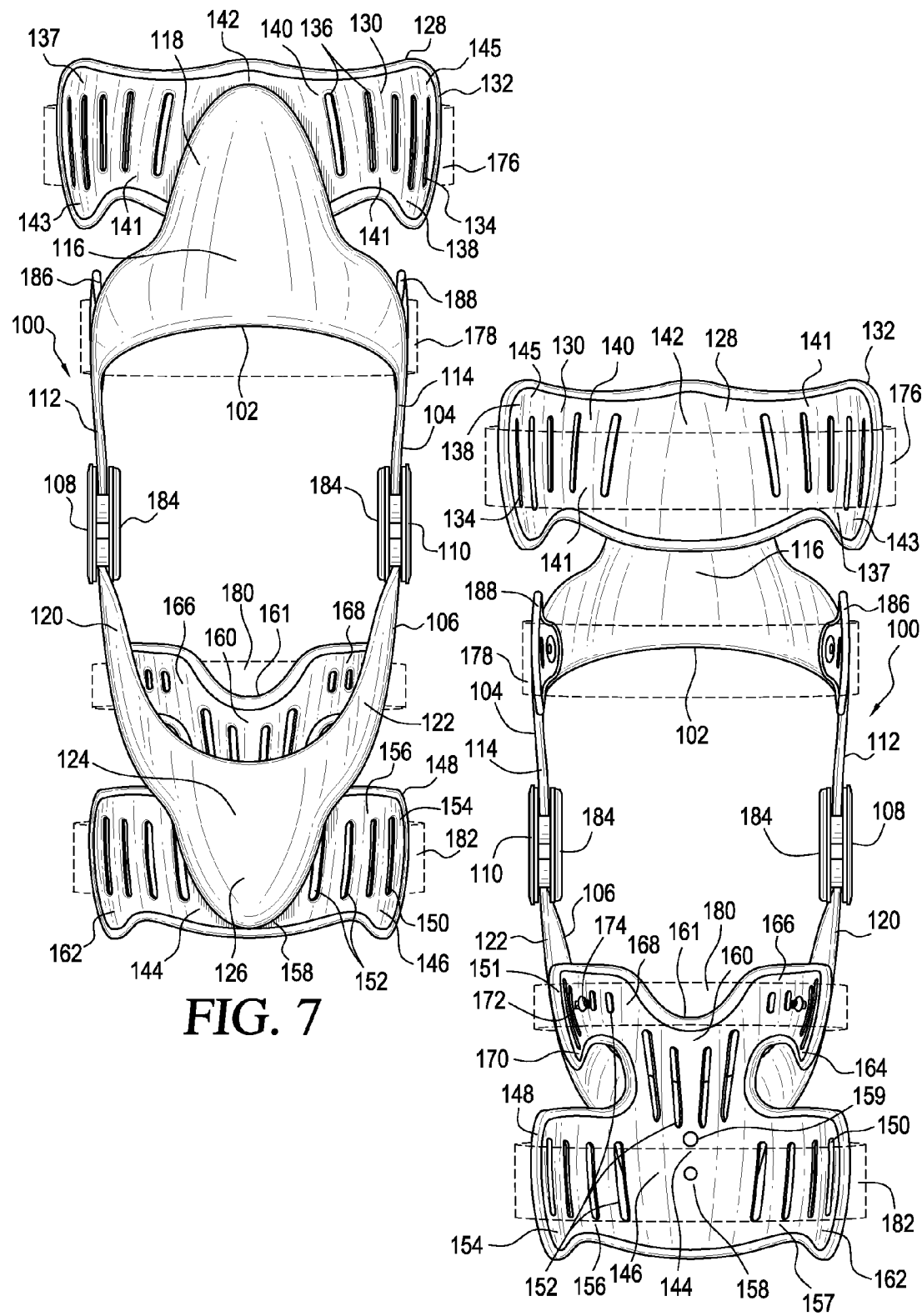

ORTHOPEDIC COMPONENT FOR USE WITH AN ORTHOPEDIC BRACE

TECHNICAL FIELD

The present invention generally relates to orthopedic devices or braces, and more particularly to an orthopedic brace including flexible and ventilated components or subshells possessing discrete regions having superior pressure-relieving properties and different degrees of flexibility.

BACKGROUND

Orthopedic braces comprise a broad range of structures and devices used for supporting or stabilizing a joint when worn on the body of a user. Orthopedic braces may serve in either preventative or remedial roles. In the preventative role, the brace can provide additional support, stability and protection to a healthy joint so as to prevent or minimize injury to the joint due to undue stress. On the other hand, in the remedial role, the brace can support and strengthen a weakened joint due to injury or infirmity, and thereby reinforce the joint to prevent further injury, or correct or assist the infirmity.

Typically, orthopedic braces include a frame that comprises at least one support member. When there are multiple support members, the brace may include rotational hinges that assist and control movement of the limb. Suitable straps may be used to maintain the brace on the limb, and other features such as pads may be used to relieve pressure of the brace on the limb and surrounding areas.

A predominant type of orthopedic brace is a knee brace. Knee braces are used to stabilize the knee by preventing excessive movement of the knee, or to facilitate movement of the knee. Many braces comprise a frame and have hinges located on at least one of the lateral and medial sides of the knee joint. Straps are used to secure the brace to the leg or knee. An injured knee can be fit with an "off the shelf" brace or a "custom-fit" brace, with the selection of the type of brace depending on the size and shape of an individual's leg.

Many knee braces are designed to reduce knee instability following an injury, fatigue or to treat impairment of the knee, particularly if the knee has damaged ligaments. Braces may be recommended for walking, skiing, running, twisting, pivoting, or jumping activities. In addition to providing increased stability to the knee, braces may also decrease the risk of injuring the knee or leg, or provide corrective assistance to the knee. One way of protecting the knee is by including attachments such as a patella protector assembly which may be secured onto the brace and configured to operate to protect the patella impact during physical activities.

In order to maximize its supportive, protective and comfort aspects, it is desirable that a knee brace securely and precisely fit the leg of the wearer. While custom-fit braces are made to closely conform to the exact geometry of a leg of a wearer, it is common for the geometry of the leg to change over time thereby requiring even a custom-fit to be able to accommodate a variety of geometries of the leg. As for off-the-shelf braces, these braces must be configurable to generally accommodate a variety of leg geometries irrespective of the particular geometry of a leg.

In recognizing the need for effective knee braces, various knee braces have been introduced into the marketplace. Such knee braces, however, have generally comprised relatively heavy, bulky apparatuses that fail to provide ventilation and evenly distribute pressure from the brace on the leg of the wearer. Moreover, many contemporary braces are deficient in that the braces are constructed in a manner that do not consistently provide or lack adjustment features for forming a firm, comfortable and secure interface between the leg and knee of the wearer and the brace. As a result of these drawbacks, many knee braces detract from the user's endeavor.

The features of the present invention are provided in recognition of the need for orthopedic braces and components for use therewith that are adjustable in both custom-fit and off-the-shelf braces so as to achieve superior functional performance characteristics while being comfortable to the wearer when worn. This recognition is realized with the invention described hereinafter.

SUMMARY

In accordance with one of the exemplary embodiments described herein, this disclosure describes an orthopedic component for use with an orthopedic device or brace. The orthopedic component includes a resilient first shell body defining front and rear surfaces, and a perimeter edge portion surrounding the perimeter of the first shell body. The edge portion has greater flexibility than the first shell body.

The perimeter edge portion defines a lip extending over a portion of at least one of the front and rear surfaces. The lip is spaced a distance above the first shell body so as to define a clearance between the first shell body and the lip. The first shell body may have a predefined curvature, and the perimeter edge portion may define an end portion having a reduced, transitional thickness and extending beyond the periphery of the first shell body.

The first shell body may define an elongate slot, and the orthopedic component may further comprise a border edge portion integrally connected to the first shell body and surrounding the slot. The border edge portion may have a greater hardness than the first shell body. The first shell body may also define reinforcement elements protruding outwardly from one of the surfaces thereof such that the reinforcement elements are located at or near opposed end portions of the slot. The orthopedic component may also comprise a border edge portion which is integrally connected to the first shell body and surrounds the aperture. The border edge portion may have greater hardness than the first shell body.

In a variation of the first shell body, the first shell body may define an aperture, and the orthopedic component further comprises a fastener guard located around the aperture and having at least one resilient flexion feature extending from and spaced over one of the surfaces of the first shell body.

The orthopedic component may also comprise a second shell body such that the first and second shell bodies are connected to one another via a connective portion integrally formed from the peripheral edge portion. The connective portion may have greater flexibility than the first and second shell bodies and a thickness less than the combination of the peripheral edge portion and the first shell body.

The peripheral edge portion may extend about the periphery of the second shell body and form the lip and clearance from a surface of the second shell body. The connective portion may define a transitional, beveled section leading to a portion of decreased thickness as compared to portions of the peripheral edge portion corresponding to the lip.

The orthopedic component may further include a padding liner having substantially a same shape and size as the first shell body, and a same thickness as the clearance. The padding is retained within the pocket by the resiliency of the lip of the peripheral edge portion which extends over a portion of a surface of the padding liner and urges the padding liner against the first shell body. The padding liner may be solely retained within the pocket by the resiliency of the lip. The first shell body may define a plurality of openings and the padding liner may have a ventilated structure such that the combination of the first shell body and padding liner permits air circulation therethrough.

The features described herein in connection with the exemplary embodiments enable significant improvements to orthopedic devices, such as knee braces, in the way of improved stability, fit, weight, comfort and appearance. The subshells allow for a considerable reduction in weight and provide close compliance to the anatomy of the wearer. This results in a comfortable device that is particularly less bulky and easily ventilated and further allowing for better suspension on the leg anatomy. These advantageous features combine to form a streamlined device allowing the wearer greater freedom, flexibility and stability of the anatomy when the device is worn. For example, the construction of these features allows for a device in which straps may be mounted under frame elements for better soft tissue containment and a more intimate fit. Further, the subshells have an appearance in combination with an overall streamlined set of features, which make the device more enticing to wear over prior art braces so as to better assure patient compliance in wearing the brace.

These and other features, aspects, and advantages of the present invention will become better understood with regard to the following description, appended claims, and accompanying drawings.

BRIEF DESCRIPTION OF THE DRAWINGS

FIG. 2 is a front elevational view of the brace according to FIG. 1.

FIG. 3 is a rear elevational view of the brace according to FIG. 1.

FIG. 7 is a front elevational view of the brace according to FIG. 6.

FIG. 8 is a rear elevational view of the brace according to FIG. 6.

DESCRIPTION OF VARIOUS EMBODIMENTS

A. Overview

Figure 1:
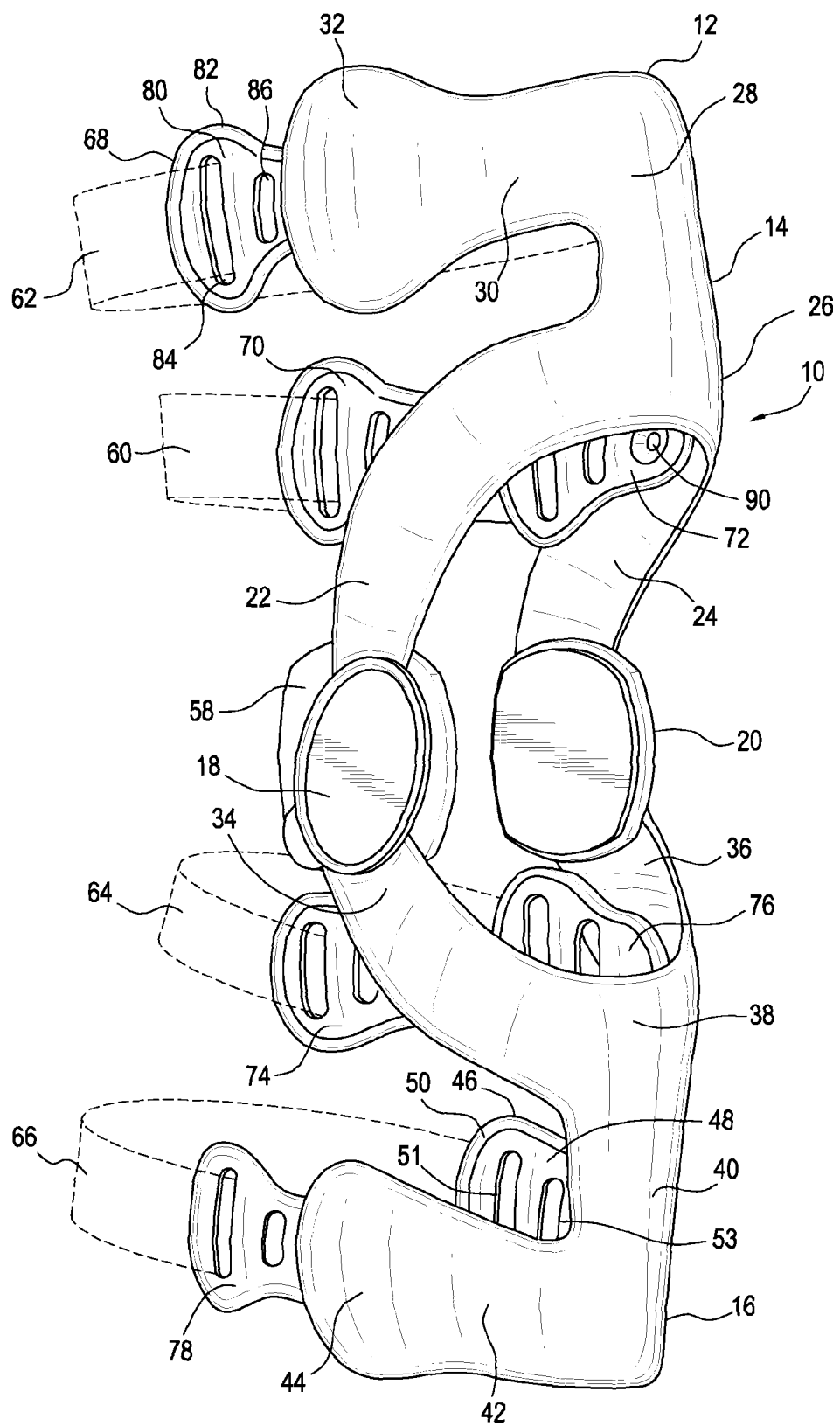
FIG. 1 is a perspective view of an embodiment of an orthopedic brace.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Environment and Context of Embodiments

Numerous orthopedic brace embodiments and components (e.g., subshells and strap retainers) for use therewith are described herein, with particular focus given to braces and components directed to the knee joint and surrounding areas. The orthopedic brace embodiments may serve in protective, preventative or remedial capacities. While the orthopedic brace is described within the context of a preferred embodiment that is directed to securing the knee joint, many of the features described herein may be extended to orthopedic braces and components that secure other joints and body parts, such as the wrist, elbow, shoulder, ankle and neck.

The brace embodiments and components for use therewith may be dimensioned to accommodate different types, shapes and sizes of human joints and appendages. In addition, embodiments may be modified to orient principal forces exerted by strap systems of the embodiments at any desirable location to secure the brace onto a leg in order to stabilize the knee.

The knee joint comprises two joints, lateral and medial, between the femur and tibia, and one arthrodial joint between the patella and femur. The primary movements of the knee comprise flexion, i.e., rearward rotational movement of the tibia relative to the femur, and extension, i.e., forward rotational movement of the tibia relative to the femur.

For explanatory purposes, each orthopedic brace embodiment or component thereof described herein may be divided into sections which are denoted by general anatomical terms for the human body. Such anatomical terms are provided to distinguish various elements of the brace embodiments from one another, but which are not to be considered to limit the scope of the invention.

Each of these terms is used in reference to a human leg, by way of example, which is divided in similar sections with a proximal-distal plane generally extending along the meniscus of the knee between the femur and tibia. The terms "proximal" and "distal" generally refer to locations of the brace that correspond to the location of leg relative to the point of attachment of the leg to the body. The terms "upper" and "lower" may be used in combination with "proximal" and "distal" to connote gradations in location of "proximal" and "distal." The location at where the brace corresponds to the knee joint is used herein to generally delimit the proximal and distal sections of the brace.

The embodiments of the knee brace can also be considered to fall within "anterior" and "posterior" sections by an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The terms "inwardly" or "inner" commonly used herein to distinguish the side of the brace that may be directed to the posterior side of the brace and specifically adjacent to the leg of the wearer of the brace. Contrariwise, the term "outwardly" or "outer" are used to denote the side of the brace that is opposite to the inwardly side.

The terms "medial" and "lateral" are relative terms that are generally understood as indicating location near the midsaggital plane or midline. Therefore, elements that are located near the midline are referred to as "medial" and those elements that are further from the midline are considered to be "lateral." The term "central" is used to denote the area along the midline of a joint thereby dividing and sharing regions of the medial and lateral regions.

From these terms, it follows that the anterior section of the brace has the following quadrants: (I) proximal-medial, (II) distal-medial, (III) distal-lateral, and (IV) proximal-lateral. The posterior section of the brace has the following quadrants: (V) proximal-medial, (VI) distal-medial, (VII) distal-lateral, and (VIII) proximal-lateral. Structural members and features thereof will fall within one of the quadrants is specifically referenced in relation to such quadrant, either in its entirety or partially.

The terms "rigid" and "flexible" are repeatedly used herein to distinguish characteristics of portions of the brace. The term "rigid" is intended to denote that the frame is generally devoid of flexibility. Within the context of frame members that are "rigid," it is intended to indicate that they may break if bent with sufficient force. On the other hand, the term "flexible" is intended to denote that features are capable of repeated bending. The term "resilient" is used to qualify such flexible features as generally returning to the initially molded shape with permanent deformation.

The anatomical and characteristic terms described herein are not intended to detract from the normal understanding of such terms as readily understood by one of ordinary skill in the art of orthotics. Moreover, the elements of the embodiments described herein are intended to embrace embodiments that generally correspond to the aforementioned anatomical sections. In other words, it is understood that the elements of the brace embodiments described herein may deviate from falling exactly within the confines of the aforementioned anatomical sections.

C. Various Embodiments of the Orthopedic Brace and Components for Use Therewith In observing FIGS. 1-3, an embodiment of the orthopedic brace is shown and generally designated 10. For explanation purposes, the orthopedic brace 10 is a knee brace configured for securing to a right leg of a user. Nonetheless, it is readily apparent to the skilled artisan from the discussion herein that the orthopedic brace and particular features thereof of the present invention may be adapted to be secured to a left leg or other parts of the body to treat skeletal joints apart from the knee.

The orthopedic brace 10 comprises a substantially rigid frame 12 including proximal and distal frame assemblies 14, 16, a substantially flexible distal subshell 46, lateral and medial central joints 18, 20, substantially flexible strap retainers 68, 70, 72, 78, padding, and a plurality of straps. For simplification, the brace embodiments shown herein are depicted without their specific straps and padding. A more detailed description of possible configurations of the straps and the padding that may be used in accordance with the orthopedic brace described herein is provided in U.S. patent application publications 2006/0135900 and 2007/0185425, owned by the assignee of this disclosure and incorporated herein by reference.

The frame 12 includes a proximal frame assembly 14, a distal frame assembly 16, and lateral and medial joints 18, 20. The proximal frame assembly 14 comprises in combination a lower proximal-lateral longitudinal support 22, lower proximal-medial longitudinal support 24, proximal-central support 26, proximal-central stem 28, and upper proximal-lateral support 30. The distal frame assembly 16 comprises in combination an upper distal-lateral support 34, upper distal-medial support 36, distal-central support 38, distal-central stem 40, and lower distal-lateral support 42.

The proximal and distal frame assemblies 14, 16 preferably have arcuate configurations which are arranged to accommodate the contours of a leg. For example, the upper proximal-lateral support 30 and the lower distal-lateral support 42 each include cuff sections 32, 44, respectively, that are intended to conform to lateral aspects of the proximal and distal portions of the leg when the brace is placed on the leg of the user. According to the embodiment of FIGS. 1-3, the proximal and distal frame assemblies do not yield to the contours of the leg but instead are preformed to a particular shape that accommodates the leg. When worn, the proximal and distal frame assemblies 14, 16 are intended to be shaped so as to closely trace and secure to the leg.

The proximal and distal frame assemblies 14, 16 are each preferably constructed from a unitary or continuous rigid piece of material. In other words, by way of example in reference to the proximal frame assembly 14, the lower proximal-lateral longitudinal support 22, lower proximal-medial longitudinal support 24, proximal-central support 26, proximal-central stem 28, and upper proximal-lateral support 30 continuously merge into one another. The distal frame assembly 14 is similarly configured to the proximal frame assembly 16.

The frame 12 is preferably characterized herein as being substantially rigid. The rigidity of the frame is generally the result of both the material from which the frame is constructed and its geometry. The material and geometry of the proximal and distal frame assemblies 14, 16 are generally rigid along the entirety of their length such that rigidity of the frame assemblies has a generally high and uniform rigidity. Exemplary materials that may be used for constructing the frame include metals such as aluminum, titanium, and steel, thermoset resin composite systems including glass or carbon fibers, and thermoplastics that have been rendered rigid by way of material composition and geometry of the frame members.

It will be noted that the requirement that the frame 12 has substantially rigid properties is provided only as an exemplary configuration. It will be noted that the frame may have flexible properties, and may further be provided in discrete segments such that the proximal and distal frame assemblies are segmented as opposed to continuous, and may be connected to one another by suitable hinges, fasteners or other suitable elements.

The proximal and distal frame assemblies 14, 16 are connected to one another by the lateral and medial joints 18, 20. The lateral joint 18 connects the lower proximal-lateral longitudinal support 22 to the lower distal-lateral longitudinal support 34, and similarly the medial joint 20 connects the lower proximal-medial longitudinal support 24 and the upper medial-upper longitudinal support 36. The ends of the longitudinal supports 22, 24, 34, 36 are configured to cooperatively engage the lateral and medial joints 18, 20.

The lateral and medial joints 18, 20 are preferably rotational hinges, which rotationally connect the proximal frame assembly 14 to the distal frame assembly 16. The lateral and medial joints 18, 20 enable rotational displacement of the proximal-lower lateral and medial longitudinal supports 22, 24 between positions of extension and flexion. Suitable condoyle pads 58 may be used to cover at least portions of the lateral and medial central joints 18, 20, and may be configured to be removable and replaceable.

The substantially flexible distal subshell 46 secures to a posterior surface of the frame 12. The distal subshell 46 connects to the distal-central support 38 and the distal-central stem 40 via fasteners through apertures 92. The distal subshell 46 projects and depends freely from the frame 12 so as to extend into the medial side of the brace and be located lower from the distal medial longitudinal support 36. In effect, the distal medial subshell 46 is a counterpart to the lateral lower support 42; however it is significantly flexible, resilient and durable.

These features and those described that follow, are not limited to a "distal" subshell, but may be extended to a subshell located at any location in an orthopedic device. In other words, any of the subshells described herein are not limited in structure and location with regard to their exemplary embodiments; they may be modified and located at any suitable location in an orthopedic device.

According to the embodiment of FIGS. 1-3, the distal subshell 46 is defined, at least in part, by a main body 48. The main body 48 includes a central end region 52 that secures to the distal-central support 38 and the distal-central stem 40, a medial end region 56, and an intermediate section 54 that connects the central end region 52 to the medial end region 56. As depicted in FIGS. 2-3, the intermediate portion 54 may be narrower than the central and medial end regions 52, 56. The medial end region 56 is generally enlarged so as to conform to the medial aspect of the lower portion of the user's leg when the orthopedic brace is placed upon the leg of the user. A significant advantage to the subshell is that it can be sized to cover a broad portion of the anatomy of the leg to more effectively and comfortably secure (by distributing forces) the brace to the leg without appreciably adding to the weight of the brace.

The distal subshell 46 has a ventilation feature 53 in the form of elongate slots that may extend or be located anywhere on the main body 48 and be arranged in a configuration which facilitates the passage of air through the subshell 46. At least one of the slots 53 defines a strap slot 51 that may be used to secure a strap 66 thereto that connects to a corresponding side of the lower distal-lateral support.

The distal subshell 46 may be used in combination with an apertured or ventilated padding that may be shaped to accommodate the subshell, or have any other suitable configuration defining a padding feature. While a preferred type of padding is described by way of the spacer elements in U.S. patent application publications 2006/0135900 and 2007/0185425, other padding can be used that may or may not be ventilated.

In the embodiment of FIGS. 1-3, the subshell 46 is substantially more flexible than the substantially rigid frame 12. For example, while the rigid frame 12 does not yield to the leg when worn, the subshell 46 is flexible so as to bend so as to conform to the leg thereby improving comfort to the wearer and further distributing forces exerted onto the leg.

A distinguishing feature of the subshell 46 is that it includes a pressure-relieving perimeter edge portion 50. The pressure-relieving perimeter edge portion 50 is distinguished from the main body 46 in that it preferably has a softer texture. More specifically, the perimeter edge portion 50 has a hardness that is lower than the hardness of the main body 46.

According to one variation, the main body 46 and the perimeter edge portion 50 are formed from materials having different hardnesses. In this variation, the main body 46 and the perimeter edge portion 50 are injection molded thermoplastics that are integrally molded together. An exemplary combination of materials comprises thermoplastic polyurethane elastomers sold under the name ELASTOLLAN by BASF group.

In making the subshell of this variation, the main body is first fabricated by being formed by a first mold. A first material, such as ELASTOLLAN S60D53N, is injected into the mold so as to result in the formation of the main body. The molded main body is then transferred to another, larger second mold which forms the shape of the definitive subshell including the perimeter edge portion. The main body is secured and centered in the second mold. A second material, such as ELASTOLLAN C60A10W, is injected into the second mold so as to contact the main body and form the perimeter edge portion therearound. Due to the similarity in composition of the first and second materials, the second material of the perimeter edge portion bonds to the first material of the main body as it is formed in the second mold. In this variation, the first material has a hardness that is greater than the second material.

A significant advantage to this variation of the subshell is that the combination of a flexible subshell with or without a soft perimeter edge portion provides a substantially comfortable feature to the orthopedic brace. Unlike conventional braces, the distal subshell yields to the shape of the leg while retaining the strap and the perimeter edge portions relieves pressure along the edges of the subshell. This allows for better soft tissue containment and an intimate fit thereby providing the wearer enhanced freedom and flexibility when wearing a device having the subshells. This also leads to better suspension of the device having the subshell on wearer's anatomy, which assists in maintaining the device in the position to optimize bracing. Added with the ventilation feature, for example the type described in U.S. patent application publication 2006/0135900, the orthopedic brace provides a feature that reduces bulk weight and size of known subshells or braces in general, and facilitates breathability of the brace.

Another advantage to this variation of the subshell results in eliminating the need to configure the subshell in a manner that would include portions for receiving the perimeter edge portion. As such, the main body may be molded with a perimeter edge portion that does not include ledges, slots or grooves for receiving the subsequently molded second material forming the definitive perimeter edge portion. This provides a generally continuous structure without gaps, raised areas, sharp edges and other protuberances or recesses that may cause discomfort to the wearer of the brace.

Another advantage to this variation of the subshell is that the subshell and the perimeter edge portion, being continuous with the main body, may be pigmented in a different color from the main body. This provides an appearance resulting in a piping around the periphery of the subshell which conveys a visually pleasing appearance. For example, the first material used for forming the main body of the subshell may have a black pigment, whereas the second material used for forming the perimeter edge portion may have a gray pigment.

The appearance of the subshells may be important, in additional to their beneficial functional characteristics, in that they may make the brace more enticing to wear so as to assure better patient compliance of an orthopedic device having the subshells. As readily apparent from the description on the structure of the subshells, they allow for more streamlined orthopedic devices due to their thin profile and their ability to sufficiently conform to the anatomy of the wearer while assisting to provide superior suspension of the device on the wearer. Moreover, the ornamental appearance, made possible in part by the piping and the slots, make it more desirable for the wearer to wear the device over orthopedic devices having less than desirable aesthetic qualities. This in turns provides the medical professional more assurance that the wearer will more fully comply with the treatment prescriptions or requirements the device is intended to treat.

Yet another advantage to this variation of the subshell is that the strap slots may also include a perimeter edge portion that is formed from a material that is substantially harder than the material of the main body. Such a material, as with the first and second materials of this variation, may again be of a similar nature to the first and second materials, but of a composition that has a greater hardness, so as to continuously bond with the subshell and to form an integral subshell structure. This harder material surrounding a main body is particularly useful to provide enhanced durability (i.e., when a strap is arranged to rub against the harder material).

It will be noted that it is preferable that the material of the main body of the subshell has a toughness that can permit a strap to be secured directly therewith. Such a feature therefore allows the subshell to not only serve as a bracing feature for the orthopedic brace, but also eliminates the need for additional strap retainers to be secured to the subshell.

While similar materials are described in connection with this variation, it will be noted that dissimilar materials may also be used. For example, polyethylene, polyurethane and other thermoplastics may be used for forming the main body, and suitable materials such as vinyl, rubber or thermoplastic elastomers may be used for forming the perimeter edge portion. Other methods for forming the main body with the perimeter edge portion may be found in U.S. Pat. Nos. 5,445,602 and 5,716,335, incorporated herein by reference. Moreover, a soft flexible perimeter edge portion may be mechanically adhered, such as an adhesive, to a subshell having ledge, slotted or groove portions upon which the perimeter edge portion may be adhered that does not interlock with any structure of the main body of the subshell.

It will be pointed out that the perimeter edge portion is merely an exemplary form of overmolding over a main body or base shell. Indeed, the main body or base shell may include other areas of overmolding, such as a center portion filling in an opening in the base shell, to provide pressure relieving characteristics to a shell. In another example, the material surrounding and forming slots defining a ventilation feature of the subshells may comprise an overmolded material that has different properties than a main body or base shell. Such properties may not necessarily comprise those having less hardness than the main body or base portion; for example, such properties may be those having a greater resiliency and hardness than the main body or base portion.

The strap retainers 68, 70, 72, 74, 76, 78, are formed substantially as the distal subshell 46 in that the strap retainers, by way of strap retainer 68, are substantially flexible and are particularly mounted via a fastener that extends through fastening aperture 90 of the strap retainer and secures to the inwardly facing side of the frame 12. The strap retainer 68 also includes a main body 80 formed from a first material that has a greater hardness than a perimeter edge portion 82. The strap retainer 68 also includes a strap slot 84, and at least one ventilation feature 86 by way of a slot. The materials used for forming the strap retainer 68, according to one variation, may be the same materials used to form the exemplary distal subshell 46 (i.e., the first material for the main body 80, and the second material for the perimeter edge portion 82).

Like the distal subshell 46, the strap retainer 68 is configured to bend or conform to the contours of the leg of a wearer of the orthopedic brace. Since the materials of the strap retainer are flexible, and further because the strap retainer has a ventilation feature, the strap retainer may be sized larger than conventional D-rings or other strap retainers in orthopedic braces. This allows for the strap retainer to distribute pressure on the leg of the wearer of the brace over a greater area than in conventional devices.

Figure 13:
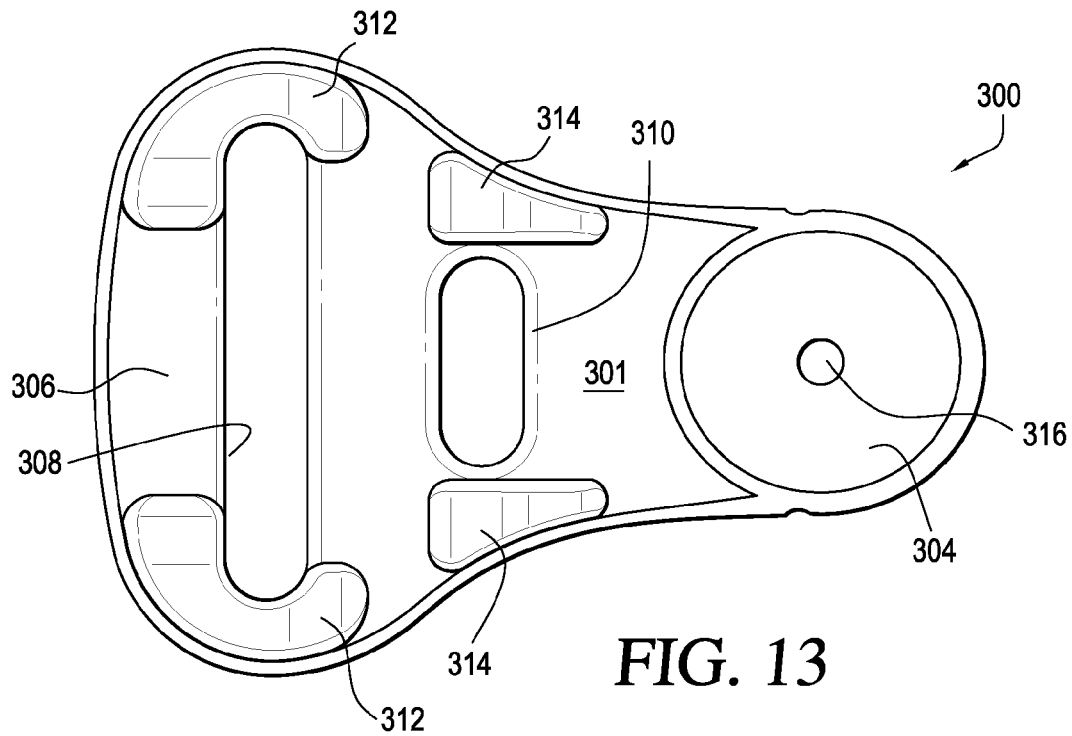
FIG. 13 is a top plan view of an embodiment of a strap retainer.

In addition to the pressure-relieving flexible perimeter edge portion, the strap retainer has a thin profile. The thin profile is partly attributed to the ability to size the strap retainer larger than conventional attachment devices due to the ventilation feature and the lightweight nature of the materials used to form the strap retainer. The strap retainer may therefore be secured on the inwardly facing side of the frame 12 which is an advantage over conventional attachment devices since mounting such devices on the inwardly facing side of the frame of a brace would likely cause discomfort to the leg of the wearer because these devices tend to be substantially rigid and bulky. The thin profile of the strap retainer is also beneficial in that it may be used with a pad, as depicted in FIG. 13, to provide an additional comfort aspect that relieves pressure.

In a variation of the distal subshell depicted in FIGS. 1-3, FIG. 4 illustrates a distal subshell 93 having a main body 94 and a perimeter edge portion 95. Unlike the distal subshell 46, this variation has a beveled perimeter edge portion 97 which corresponds to the tibia portion of the wearer. Because the tibia is prone to sensitivity, this beveled portion 97 allows for greater cushioning from its transitional profile and the soft nature of the material used to form the perimeter edge portion.

The distal subshell 93 also includes apertures 97 whereat a harder and tougher material may be used in a surrounding portion 98 about the aperture 97. This provides for greater durability when the material of the main body 94 may not be sufficiently strong to withstand repeated movement or tensioning of the subshell about a leg. The surrounding portion 98 may be molded over the main body 94 in accordance with any of the methods described herein.

Figure 4:
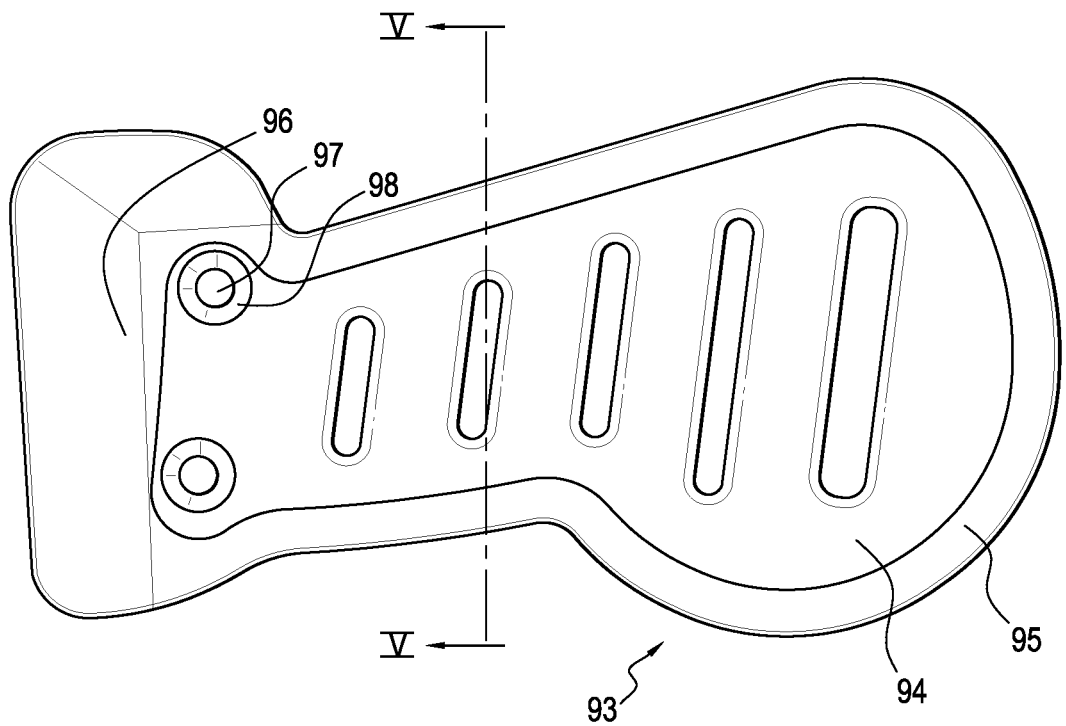
FIG. 4 is a plan view of an embodiment of a subshell used in the orthopedic brace of FIG. 1.
Figure 5:
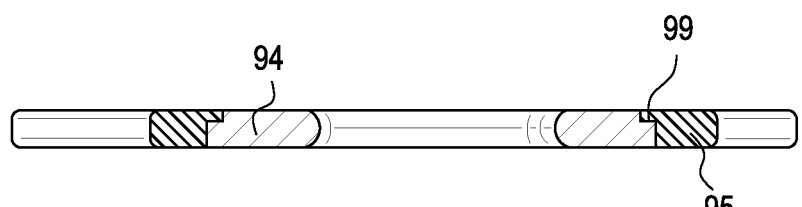
FIG. 5 is a cross-section view taken along line V-V in FIG. 4.

FIG. 5 illustrates a cross-sectional view taken along line V-V in FIG. 4. This cross-sectional view exemplifies how the main body 94 may be formed with a ledge or similar feature 99 upon which the material of the perimeter edge portion 97 is molded onto and bonds with the material of the main body 94. The ledge 99 is not limited to the configuration as shown herein but may comprise a spline, slots (through which material molded thereover interlocks), or other suitable arrangements which assure a secure interlocking of material of the perimeter edge portion and the main body.

Figure 6:
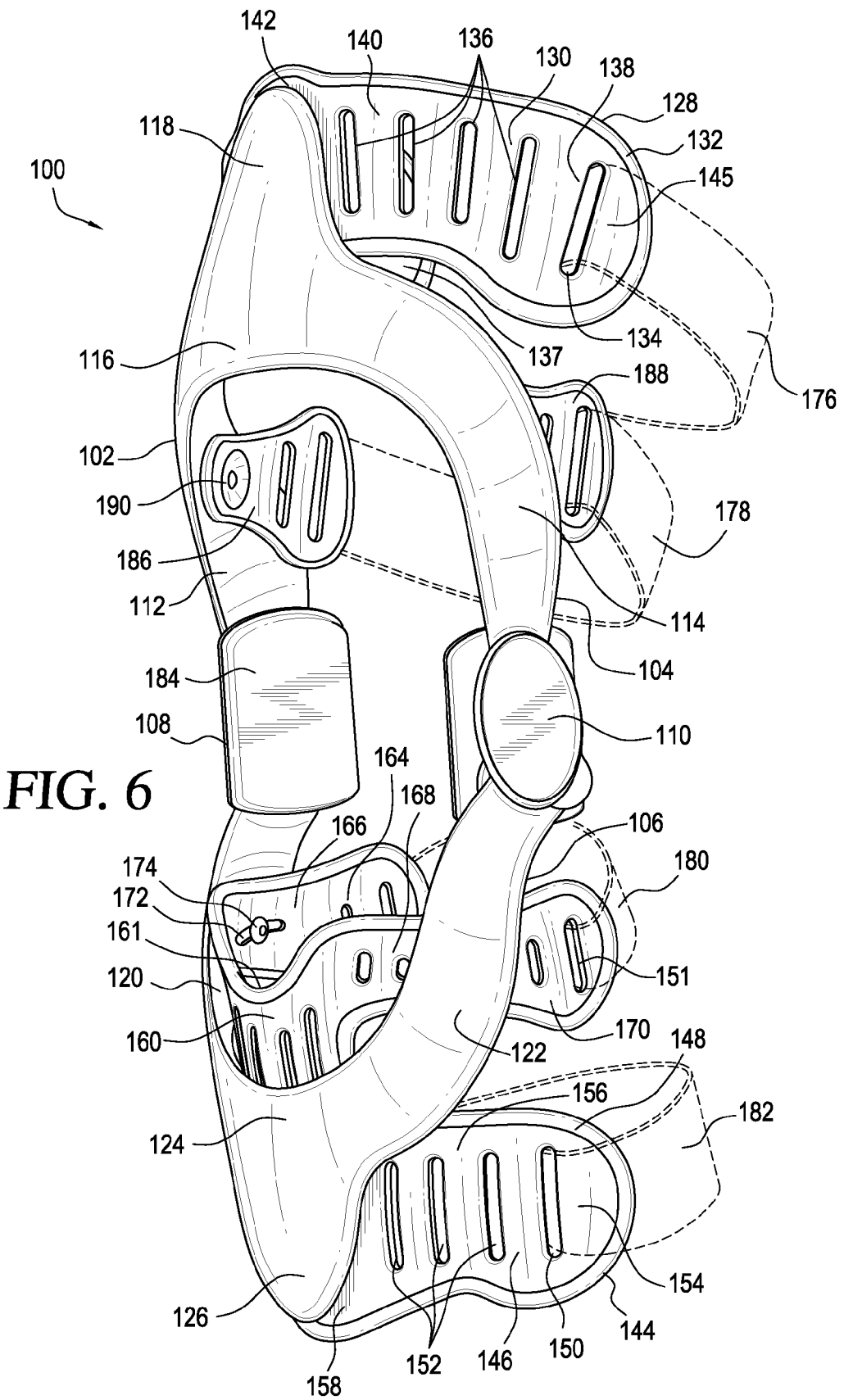
FIG. 6 is a perspective view of another embodiment of an orthopedic brace.

In another orthopedic brace embodiment 100 illustrated in FIGS. 6-8, the brace 100 may have a configuration wherein the proximal and distal subshells replace certain supports and strap retainers described in combination with the orthopedic brace 10 of FIGS. 1-3.

The frame 102 includes a proximal frame assembly 104, a distal frame assembly 106, lateral joint 108, and medial joint 110. The proximal frame assembly 104 is substantially rigid, as in the frame assembly 14 of the brace embodiment 10, and comprises in combination a proximal-lateral longitudinal support 112, proximal-medial longitudinal support 114, lower proximal-central support 116, and upper proximal-central support 118. The distal frame assembly 106 comprises in combination a distal-lateral support 120, distal-medial support 122, upper distal-central support 124, and lower distal-central support 126. The lateral and medial central joints 108, 110 operate in a similar manner to those described in connection with the embodiment of FIGS. 1-3.

Similar to the brace embodiment 10, the proximal and distal frame assemblies 104, 106 preferably have arcuate configurations which are arranged to accommodate the contours of a leg. As with the frame 12 of the orthopedic brace 10, the frame 102 is preferably characterized herein as being substantially rigid. Moreover, the proximal and distal frame assemblies do not yield to the contours of the leg but instead are preformed to a particular shape that accommodates the leg. When worn, the proximal and distal frame assemblies are intended to be shaped so as to closely secure to the leg.

The proximal and distal frame assemblies 104, 106 are also each preferably constructed from a unitary or continuous rigid piece of material. The upper proximal-central support 118, and the lower distal-central support 126, each gradually taper as they extend away from the lower proximal-central support 116, and the upper distal-central support 124, respectively. Preferably, as shown in FIGS. 6-8, the upper proximal-central support 118, and the lower distal-central support 126 have arcuate profiles so as to mitigate any sharp geometry that may pose uncomfortable to the wearer of the brace, and to ease the pressure exerted onto the femur and tibia, respectively while providing support to such areas of the leg.

As with the brace 10 of FIGS. 1-3, the brace 100 includes lateral and medial strap retainers 186, 188 that are pivotally secured via connection points 190 to the proximal lateral and medial longitudinal supports 112, 114. The strap retainers 186, 188 may have the same configuration as the strap retainers described in connection with the strap retainers of brace 10.

The brace 100 includes a proximal subshell 128 that is secured to the inwardly facing side of the frame 102 at the lower and upper proximal-central supports 116, 118. The proximal subshell 128 includes lateral and medial sections 137, 138 that generally extend from a center portion 142 that is secured to the lower and upper proximal-central supports 116, 118. The lateral and medial sections 137, 138 each include an intermediate portion 141 that connects the center portion 142 to enlarged lateral and medial end portions 143, 145, respectively.

The lateral and medial end portions 143, 145 are preferably sized larger than the intermediate portion 141 so as to embrace a greater portion of the lateral and medial aspects of the leg. The lateral and medial end portions 143, 145 each include at least one strap slot 134 for securing a strap 176 that extends between lateral and medial end portions on the inwardly facing side of the brace 100. The at least one strap slot 134 on both the lateral and medial end portions 143, 145 effectively replaces the need for any strap retainer. Due to the enlarged size of the lateral and medial end portions 143, 145 in combination with the strap 176, the pressure exerted onto a leg when the corresponding strap is tightened is able to be distributed over a larger area than is found in conventional braces.

As with the subshell 46 of the brace 10, the proximal subshell 128 includes a main body 130 and a peripheral edge portion 132. While the main body 130 is preferably flexible, the peripheral edge portion 132 is substantially flexible and has a hardness that is less than a hardness of the main body. The proximal subshell 128 may be constructed in a similar manner as the subshell 46 of the brace embodiment 10 of FIGS. 1-3.

Moreover, both the main body 130 and the peripheral edge portion 132 of the proximal subshell 128 may extend beyond the periphery of the lower and upper proximal-central portions 116, 118 so as to minimize or relieve any pressure exerted on the leg of a wearer due to the rigidity of the lower and upper proximal-central portions 116, 118.

The proximal subshell 128 includes a ventilation feature 136 that is exemplified by a plurality of slots. While other configurations may be used in addition to the slots 136, this particular configuration of FIGS. 6-8 allows for at least some of the slots to be sized and configured to also receive the strap 176 in addition to the strap slot 134 to provide greater size adjustment to the strap or allow for the strap to extend over a greater portion of the subshell. The slots 136, or other ventilation structure, may be used in combination with a textile or foam pad, or a ventilated spacer element of the type described in U.S. patent application publication 2006/0135900 and 2007/0185425. The combination of the ventilation feature with a ventilated spacer element enables the brace to be tailored so as to provide air passage through the subshell to allow for a substantially breathable portion of the brace.

While not shown, the proximal subshell may be mechanically secured to the frame 102 by suitable fasteners or adhesives. In a variation, the proximal subshell may be provided with different apertures or slots which enable the subshell to be adjustable relative to the upper frame assembly 104. Certain adjustability may be related to the height of the subshell, varus and valgus adjustment, and the ability to move freely up and down relative to the upper frame assembly when the brace is worn. Various means for providing adjustability for the proximal subshell 128 may be similar to those used in adjusting a distal or tibial subshell 144 to the distal frame assembly 106 described hereafter.

The distal subshell 144 is secured to the inwardly facing side of the frame 102 at the upper and lower distal-central supports 124, 126. The proximal subshell 144 includes lower lateral and medial sections 154, 162 that generally extend from a lower central portion 158 that is immovably secured or anchored to the lower distal-central support 126 by at least one fastener 159. The lower lateral and medial sections 162, 154 each include a lower intermediate portion 157, 156, respectively. As with the lateral and medial end portions 137, 138 of the proximal subshell 128, the lower lateral and medial sections 162, 154 each have enlarged geometry relative to the intermediate portions 157, 156 so as to embrace a greater portion of the lateral and medial aspects of the leg.

The lower lateral and medial sections 162, 154 each include at least one lower strap slot 150 for securing a strap 182 that extends between the lower lateral and medial sections on the posterior side of the brace 100. The lower lateral and medial sections 162, 154 include a ventilation feature 152 by way of a plurality of slots similar to those of the proximal subshell 128.

The distal subshell 144 also comprises an upper central portion 160 that extends proximally from the lower central portion 158, and includes a concave arcuate crest section 161 that is configured to conform to the tibia of the wearer of the brace 100. Upper lateral and medial intermediate sections 166, 168 connect respectively to upper lateral and medial sections 164, 170. Both the lateral and medial sections 164, 170 include at least one upper strap slot 151, and the ventilation feature 152. Moreover, both the upper lateral and medial sections 164, 170 are enlarged relative to the upper intermediate sections 166, 168.

Both the upper lateral and medial sections 164, 170 include at least one upper strap slot 151 that connects the upper lateral and medial sections via a strap 180. The upper lateral and medial sections 164, 170 effectively serve as both a support for the wearer of the brace and as strap retainers.

The upper lateral and medial sections 164, 170 are adjustable relative to the lower frame assembly 106, and in particular to the distal-lateral support 120, and distal-medial support 122. FIGS. 6 and 8 illustrate the upper lateral and medial sections that each define a slot 172 through which a corresponding tightenable fastener 174 extends and secures to the distal-lateral support 120, and distal-medial support 122, respectively.

Figure 9:
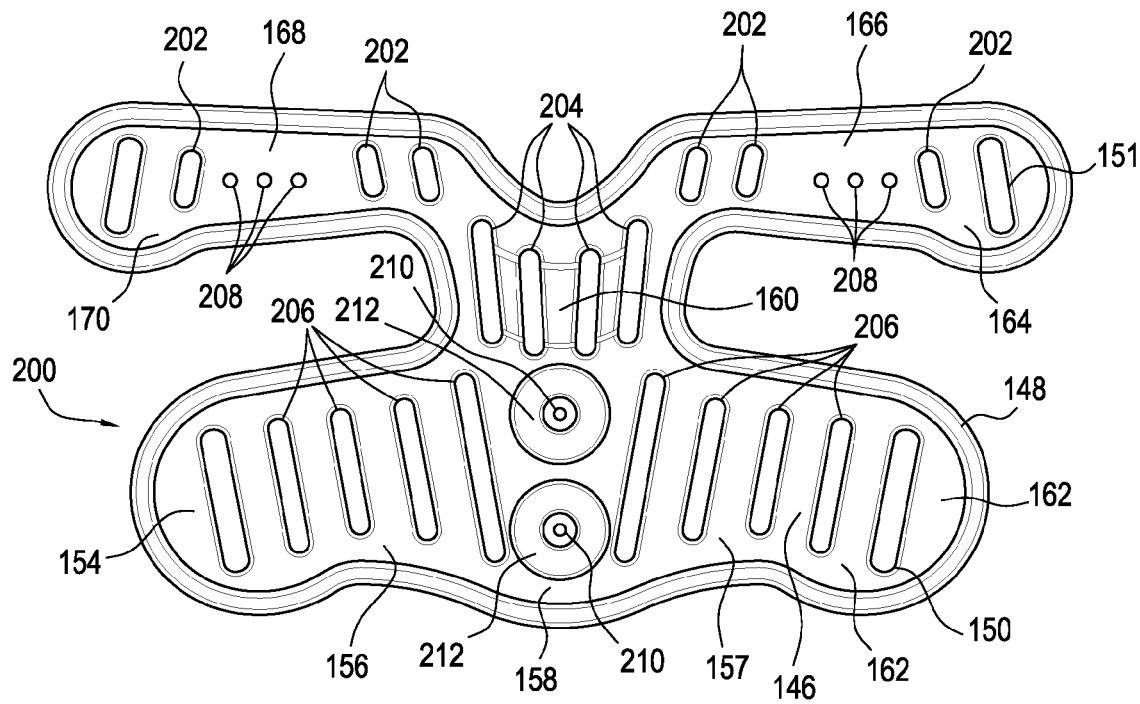
FIG. 9 is a plan view of an embodiment of a subshell used in the orthopedic brace of FIG. 6.

In a variation, FIG. 9 shows a plurality of adjustment apertures 208 which are spaced in a manner that incrementally allows for adjustment of the upper lateral and medial sections 164, 170 relative to the distal lateral and medial supports 120, 122. Such adjustment of the upper lateral and medial sections enable the adjustment of the alignment of the distal subshell and may contribute to an anterior or posterior force on the tibia. The flexible nature of the subshell allows for compliance to the leg anatomy throughout the range of adjustment.

As with the proximal subshell 128, the distal subshell 144 includes a main body 146 and a peripheral edge portion 148. While the main body 146 is preferably flexible, the peripheral edge portion 148 is substantially flexible and has a hardness that is less than a hardness of the main body. The proximal subshell 144 may be constructed in a similar manner as the subshell 46 of the brace embodiment 10 of FIGS. 1-3.

Both the main body 146 and the peripheral edge portion 148 of the distal subshell 144 may extend beyond the periphery of the upper and lower distal-central portions 124, 126 so as to minimize or relieve any pressure exerted on the leg of a wearer due to the rigidity of the upper and lower distal-central portions 124, 126.

FIG. 9 shows a variation of a distal subshell 200 that may replace the distal subshell 144 in the brace 100. The distal subshell 200 includes a plurality of differently shaped ventilation features 202, 204, 206 that correspond to different regions of the distal subshell 200. It will be understood that the ventilation features may be modified in a plurality of different configurations and are not limited to those shown or discussed herein. Of course, the ventilation features may be arranged so as to optimize or facilitate the passage of air through the subshell and any padding, liner or spacer element located between the leg and the subshell.

The distal subshell 200 also includes apertures 210 surrounded by recesses 212 for receiving fasteners that are used for securing the distal subshell 200 to the lower distal-central portion 126 of the brace 100. It will be pointed out that there are preferably, while not limited thereto, apertures and recesses for receiving fasteners defined on the distal subshell 200 that correspond to the upper distal-central portion 124. This is so the upper lateral and medial sections 164, 170 may be adjusted relative to the distal lateral and medial supports 120, 122, respectively, via the plurality of adjustment apertures 208.

Figure 10:
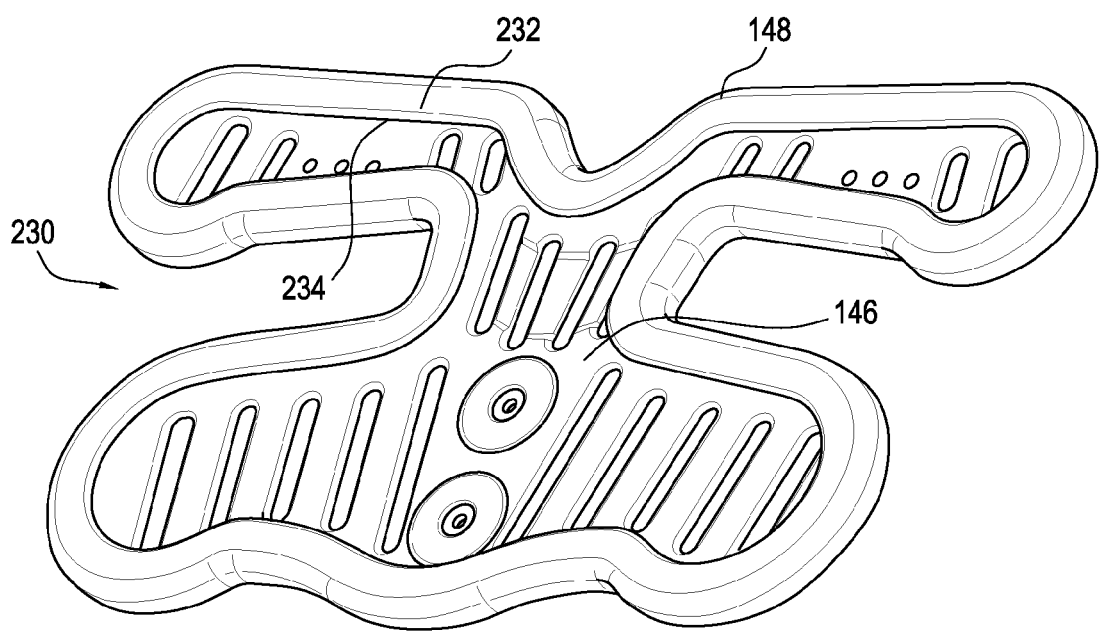
FIG. 10 is a perspective view of a variation of the subshell of FIG. 9.

FIG. 10 illustrates a variation of an orthotic or subshell 230 having a main body 146 configuration similar to the distal subshell 200. The distal subshell 230 includes a peripheral edge portion 148 that forms a lip 232 that extends over one surface of the main body 146. A groove or clearance 234 is defined between the lip 232 and the surface of the main body 146 generally about the periphery of the main body 146. While the peripheral edge portion is described as having one lip extending over a first side of the main body, it will be noted that the peripheral edge portion may form lips located over opposed sides of the main body, thereby forming clearances between the lips and such surfaces.

The combination of the groove and the lip 232, 234 defines a retaining structure or pocket for receiving a pad or spacer element having a similar profile to that of the main body 146. The peripheral edge portion is preferably formed from a resilient material so that such lips may clamp against a pad or spacer similarly shaped to the main body and placed within the confines of the pocket. This retaining structure therefore facilitates installation and removal of pads or spacer elements relative to the distal subshell 230.

The lip and groove 232, 234 conceals edges of any pad or spacer element retained thereby so as to visually hide the pad or spacer element, and further protect the edges of the pad or spacer element. This structure also advantageously makes it so that it is not necessary to use any fasteners, adhesive or other suitable means to secure pads or spacer elements to the subshell. The retaining structure exemplified in FIG. 10 may be extended to any of the subshells described herein.

Figure 11:
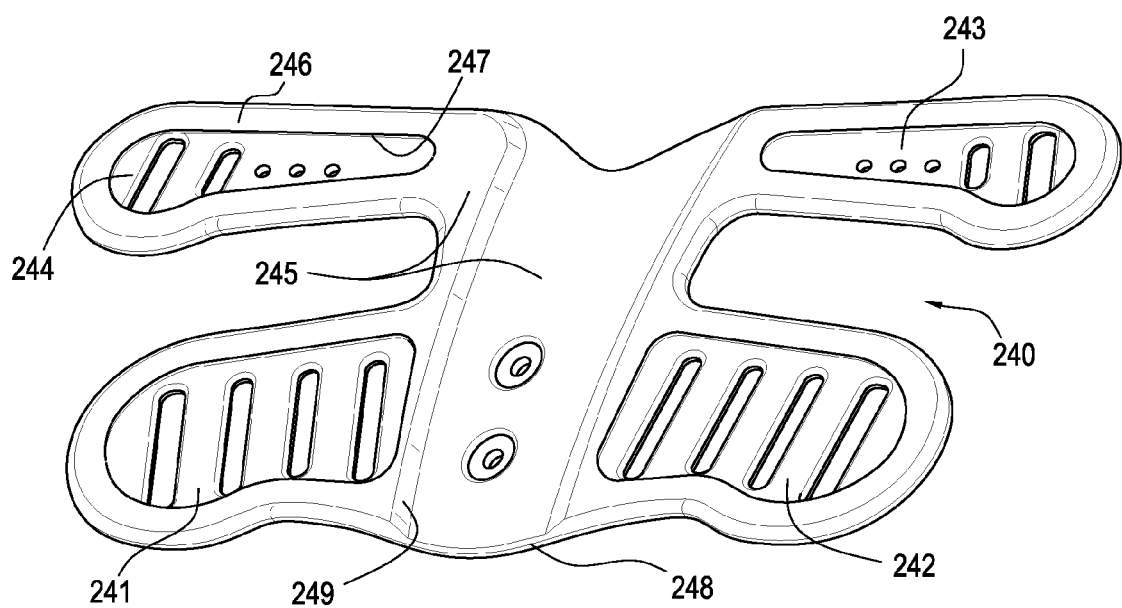
FIG. 11 is a perspective view of another variation of the subshell of FIG. 9.

FIG. 11 depicts yet another variation of an orthopedic component or subshell 240 which includes features that may be used in any of the subshells described herein. According to this variation, the subshell 240 is divided into individual shell portions 241, 242, 243, 244 which are connected to one another via a connective portion 245 formed from a material similar to the material used to form the perimeter edge portion in other embodiments described herein. The shell portions may be formed from a material similar to the material used to form the main body in other embodiments described herein. In other words, the shell portions are formed from a less compressible and tougher material than the connective portion.

The connective portion 245, as in the embodiment of FIG. 10, defines a lip 246 extending over the periphery of each of the shell portions 241, 242, 243, 244. The lip 246 is spaced above the shell portions 241, 242, 243, 244, on one side thereof, so as to define a groove or clearance 247 therebetween effectively forming a retaining structure or pocket. As with the embodiment of FIG. 10, the lip and groove 246, 247 can retain and conceals edges of any pad or spacer element retained thereby so as to visually hide the pad or spacer element, and further protect the edges of the pad or spacer element without the requirement of any fasteners, adhesive or other suitable means to secure pads or spacer elements to the subshell. It will be pointed out that the composition of the connective portion is not restricted to materials having less hardness, but it may actually have a greater rigidity or hardness than the shell portions.

Also depicted in FIG. 11 is a tibial recessed portion 248 which is defined generally at a location corresponding to the wearer's tibia. This recessed portion 248 comprises only the softer and more resilient material forming the connective portion 248. It follows that this section has a transitional, beveled section 249 leading to a portion of decreased thickness as compared to portions of the subshell having the combination of the shell portions and connective portion. This recess allows for greater cushioning and compliance about the tibia, similar to the concept used in accordance with the embodiment of FIG. 4. As with the retaining structure for a pad or spacer element, the recessed portion is preferably located on a side of the subshell which is located adjacent to the leg of the wearer. It will be pointed out that the recessed portion is not restricted to corresponding to the tibia of the wearer, but the concept of the recessed portion may be extended or placed to any location considered appropriate.

Figure 12:
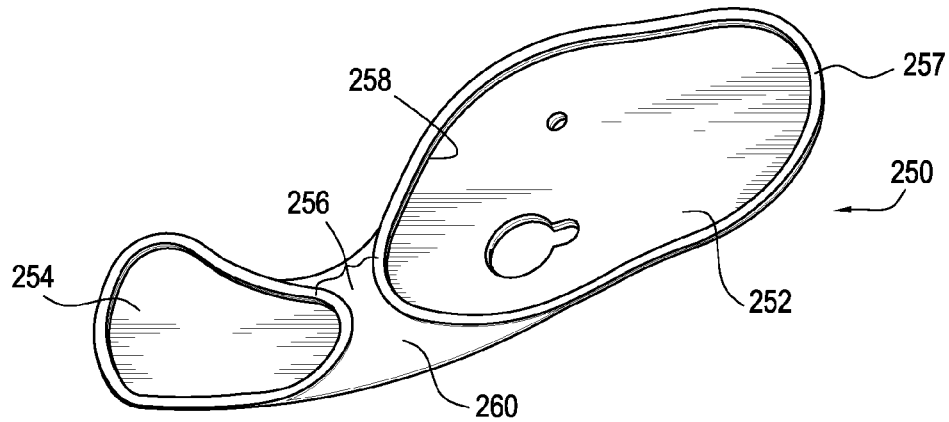
FIG. 12 is a perspective view of another embodiment of a shell employing certain features of FIG. 11.

Turning to another embodiment of an orthotic shell employing features found in part by the variations of FIGS. 10 and 11, the orthotic shell 250 of FIG. 12 exemplifies a shell construction wherein shell bodies 252, 254 are connected by connective portion 256. As with the embodiments of FIG. 11, the connective portion 256 forms a lip 257 which extends over the shell bodies 252, 254 and is spaced over such shell bodies 252, 254 on one side thereof to form a groove or clearance 258. The orthotic shell 250 is particularly in the brace described in U.S. patent application publications 2006/0135900 and 2007/0185425.

The lip 257 extends on one side of the shell 250 so that the clearance 258 defines the extension of the lip 257 relative to a central portion 260 of the connective portion 256. In other words, the central portion 260 is thinner than at the lip 257. It may also be configured thinner than the shell bodies since these shell bodies do not directly connect to one another; they are preferably connected only by the connective portion 256. The central portion 260 may correspond similarly to the tibial recessed portion 248 in FIG. 11 so as to relieve pressure at a particular portion of the tibia.

The connective portion 256 may be formed from similar materials as the perimeter edge portion of the embodiment of FIG. 10 or the connective portion of the embodiment of FIG. 11. Similarly, the shell portions 252, 254 may be formed from similar materials as the shell portions of the embodiment of FIG. 11.

It will be pointed out that while it is explained that the shell portions in FIGS. 11 and 12 do not directly connect to one another, the shells of the embodiments of FIGS. 11 and 12 may be configured so that shell portions are directly connected to one another or are formed continuously with one another. In the event the shell portions were continuously formed with one another as a single body portion, the central portion or recessed portion may be formed such that the single shell portion has a reduced thickness in comparison regions outside of such central or corresponding region.

Figure 14:
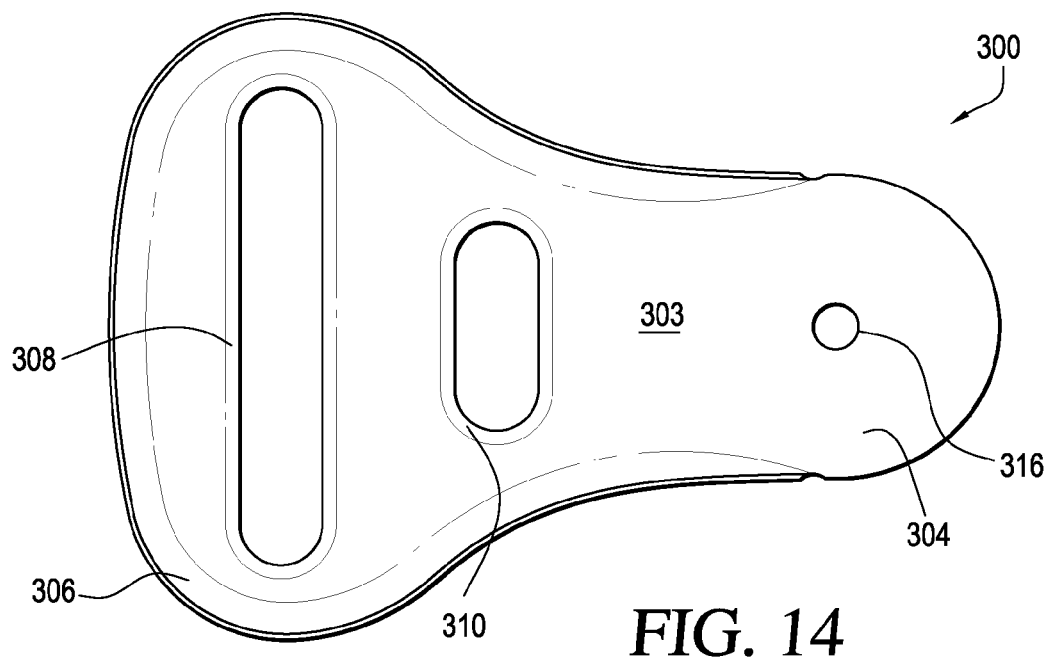
FIG. 14 is a bottom plan view of an embodiment of the strap retainer of FIG. 13.

FIGS. 13 and 14 exemplify the main body 306 of an embodiment of a strap retainer 300 prior to receiving a flexible peripheral edge portion of the type described in connection with the orthopedic braces 10, 100. In this embodiment, the main body 306 defines inwardly and outwardly facing sides 301, 303. The main body 306 includes a head portion 304 defining an aperture 316, a tail portion 306 defining a strap slot 308, and a ventilation feature 310, exemplified herein by a slot.

Reinforcement elements 312, 314 are either integrally formed or mechanically adhered to the inwardly facing surface 301 of the main body 302 and provided around at least end regions of the strap slot 308 and the slot 310. The reinforcement elements 312, 314 strengthen sections of the strap retainer so as to prevent tearing of the strap retainer and to stiffen the strap retainer at pre-selected sections. While it is preferred to provide the reinforcement elements only at the end portions of the strap slot 308 so as to allow the strap retainer to readily flex, other configurations of reinforcement elements may be used such as those that extend partially or entirely around any one of the slots or similar structure of the strap retainers. Moreover, the reinforcement elements, such as element 314, may be provided at regions of the strap retainer that are meant to bend, as depicted in the configuration of FIGS. 15 and 16.

As shown in FIG. 14, the outwardly facing surface 303 does not include reinforcement elements. However, it will be understood that reinforcement elements may be provided on the outwardly facing surface in configurations similar to those described in connection with the inwardly facing surface 301.

While the ventilation feature 310 is shown as a slot, the ventilation feature may assume a variety of configurations that do not significantly hinder the flexibility and strength of the strap retainer. Some configurations include a plurality of apertures, slots, and other suitable shapes, sizes and combinations thereof. Moreover, the ventilation feature need not include corresponding reinforcement elements.

Figure 15:
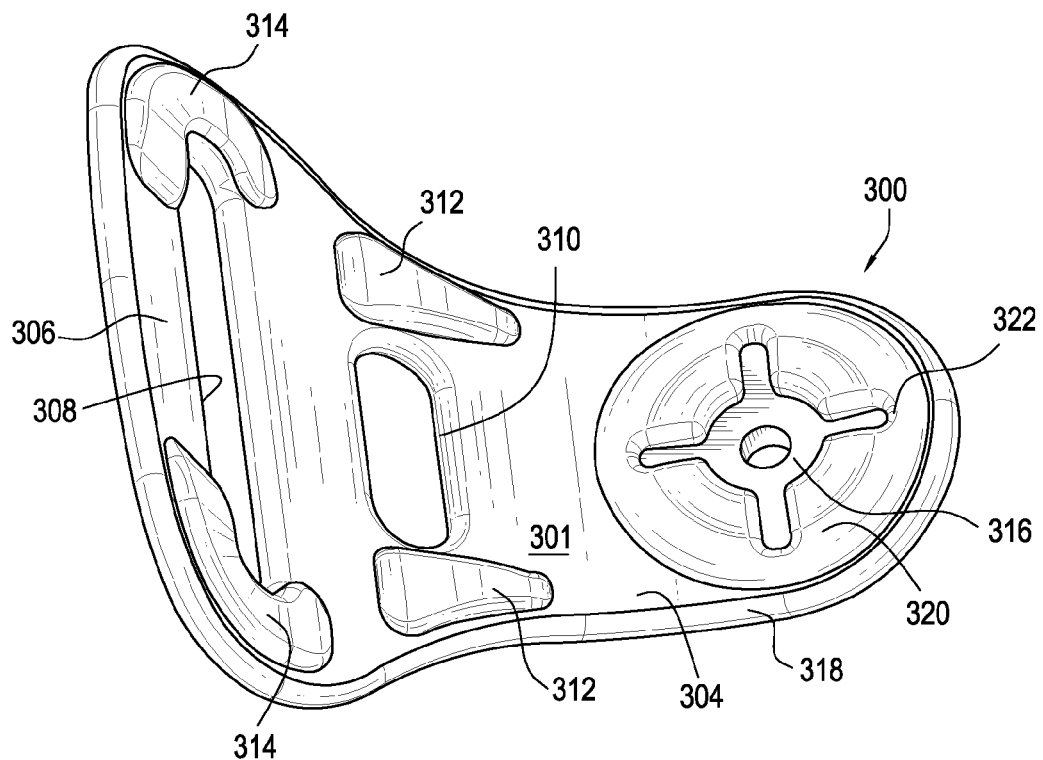
FIG. 15 is front perspective view of the strap retainer of FIG. 13 with a peripheral edge portion.
Figure 16:
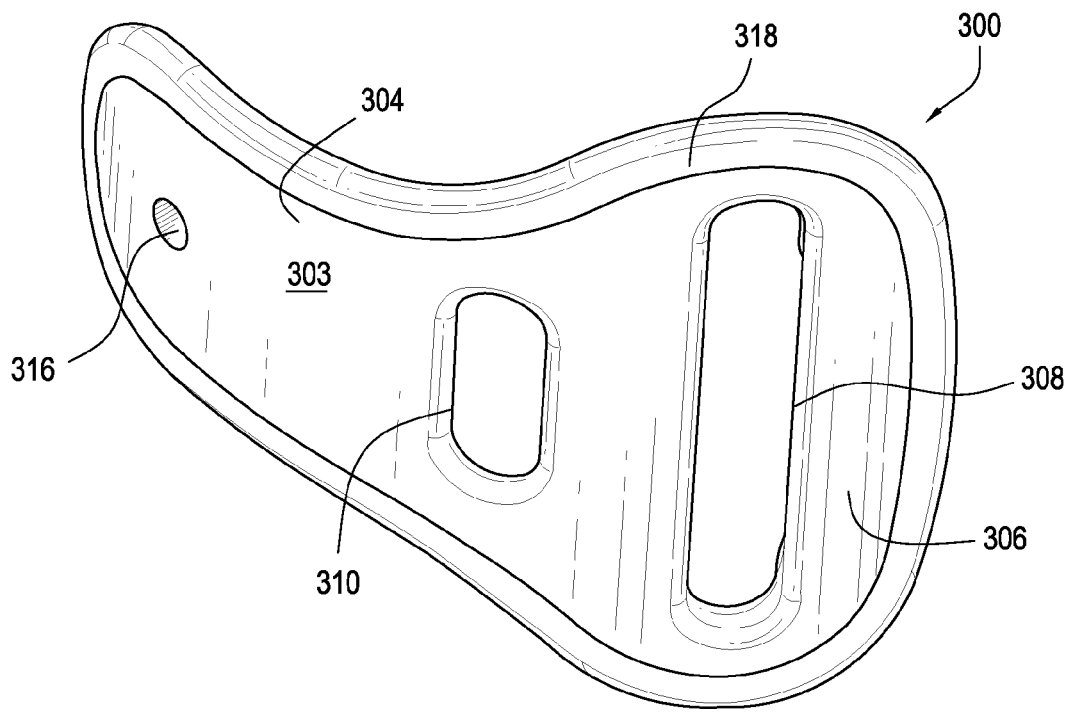
FIG. 16 is a rear perspective view of the strap retainer of FIG. 13.

The strap retainer 300 is depicted in FIGS. 15 and 16 with a peripheral edge portion 318 of the type described above in connection with the embodiments of braces 10, 100. The strap retainer 300 also includes a fastener guard 320 with flexion features 322 that cover a fastener when the strap retainer 300 is secured to a frame of the orthopedic device.

In FIGS. 15 and 16, the strap retainer 300 is formed in a curved configuration which may represent the strap retainer 300 as either in a condition wherein it is molded so as to curve, or so that it represents the strap retainer 300 when it is flexed about the leg of the wearer due to the securing of a strap between lateral and medial strap attachments.

The fastener guard 322 serves to protect the leg of the wearer of the orthopedic brace from any hard or sharp edges of the fastener. It also has cushioning and flexible properties similar to the peripheral edge portion 318. The fastener guard 320 allows for the strap retainer 300 to be mounted on the inwardly facing side of the frame without causing discomfort to the wearer of the orthopedic brace. The flexion feature 322 permits the fastener to be removed from the strap retainer and frame without destroying the strap retainer.

The fastener guard 320 may be formed from the same material that is used as the peripheral edge portion 318, and may be integrated with the main body 302 when the peripheral edge portion 318 is molded onto the main body. Alternatively, the fastener guard 320 may be formed from the same material as the main body 302, or from a different material from the peripheral edge portion 318 and the main body 302. Alternatively, the fastener guard 302 may be mechanically adhered to the main body 302.

While the strap retainer is described and shown herein in a particular geometry, it will be understood that the strap retainer may be configured in a variety of configurations. However, any such configurations must provide means for securing a strap thereto, and means for pivotably securing the strap retainer to the frame of a brace.

Figure 17:
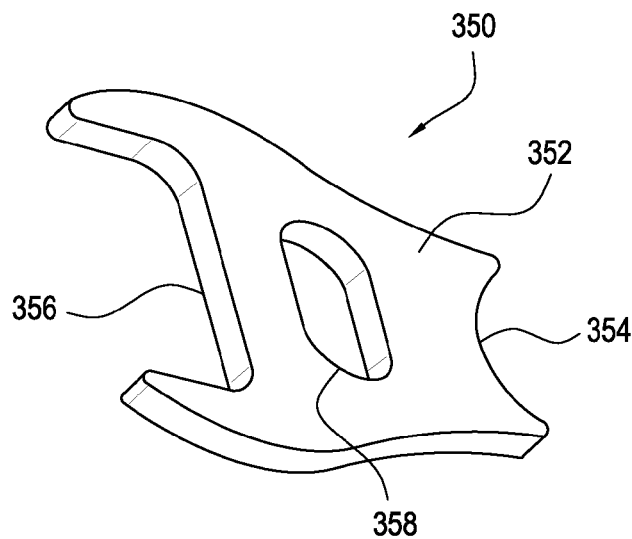
FIG. 17 is a perspective view of a strap pad for use with the strap retainer of FIG. 13.

In observing FIG. 17, a strap pad 350 may be provided that has a shape generally corresponding to the shape of the strap retainer 300. The strap pad 350 includes a main body 352 corresponding to the main body 304, a recessed head 354 that accommodates the fastener guard 320, a slot 358 that accommodates the ventilation feature 310, and a recessed tail 356 that accommodates the strap slot 308. While not shown, the strap pad 305 may also include recesses or depressions that can accommodate the reinforcement elements, and perforations by way of its inherent material composition or mechanical perforations.

The strap pad 350 is secured to the inwardly facing surface 301 of the strap retainer 300 so as to be proximate to the leg of the wearer of the orthopedic brace. The strap pad 350 may be mechanically adhered to the strap retainer 300, or removably secured via hook and loop fastener elements or other suitable elements.

Figure 18:
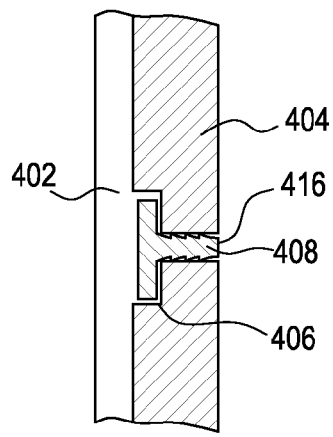
FIGS. 18 and 19 are schematic views of a fastener retainer in the frame of the orthopedic brace of FIG. 1.
Figure 19:
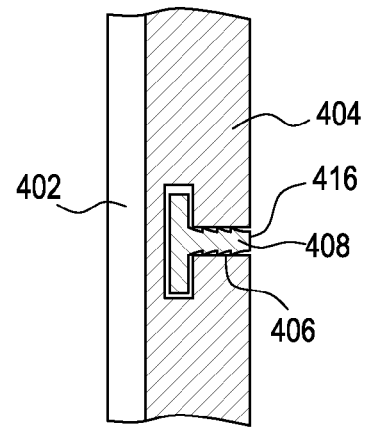
Figure 20:
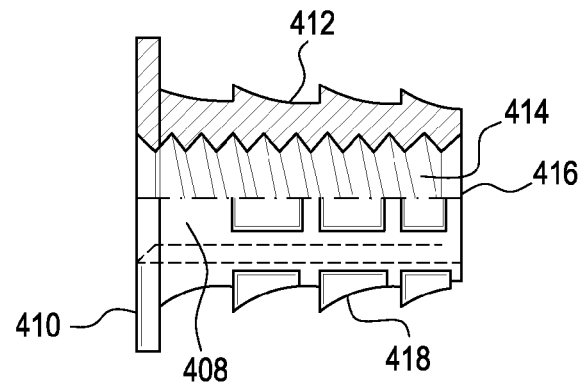
FIG. 20 is an elevational view of an embodiment of a fastener retainer.

The orthopedic brace may include fastener retainers integrated or secured within the shell, as depicted in FIGS. 18-20, for securing the strap retainers, subshells, and straps to the frame. For example, in FIG. 1, the strap 62 may have one end directly secured to the upper proximal-lateral support via a fastener 88 that is received by a fastener retainer (not shown).

In accordance with one embodiment, the fastener retainer 408 is press fitted into the frame 404 from the outwardly facing side so that an orifice 416 of the fastener retainer 408 is exposed on the inwardly facing side of the frame 404. A recess 406 may be formed within the frame thickness so as to accommodate the fastener retainer 408, or the fastener retainer 408 may be urged through the frame while the composite material cures. Upon curing of the composite material, the outwardly facing surface of the frame 404 is treated with a covering material, primer and paint (collectively represented as 402) so as to cover the fastener retainer 408 from the outwardly facing side.

In another embodiment, the fastener retainer 408 is laminated within the frame 404 thereby forming a region 406 wherein the fastener retainer 408 is contained. The fastener retainer 408 is effectively embedded within the frame 404 with only its orifice 416 being exposed along the inwardly facing side of the frame 404.

As shown in detail in FIG. 12, the fastener retainer 408 includes the orifice 416 leading to a threaded portion 414, flanged head 410, and an outer surface 412 including a plurality of cleats 418 extending therefrom. The cleats 418 serve to lock the fastener retainer 408 within the thickness of the frame 404, and to prevent the fastener retainer 408 from loosening from the inwardly facing surface of the frame 404.

The fastener retainer 408 prevents the need for any protuberances extending from either the inwardly or outwardly facing surfaces. In other words, any fasteners are preferably maintained in a low profile manner so as to minimize or avoid any hard areas on the brace that may discomfort the wearer, or snag on clothing or other items that the brace may come into contact with. Moreover, such a low profile also contributes to an overall aesthetic appearance that conceals many of the fasteners used to secure the various subshells, straps and strap retainers of the brace.

The fastener retainer may be constructed from a variety of materials such as metals and plastics that can withstand repeated securing of fasteners. Furthermore, the fastener retainer must be constructed from a material that will assure that the cleats remain embedded or secured with the frame.

In another embodiment in accordance with the invention, the brace may include a patella protector assembly using the concepts described above in accordance with the embodiments of FIGS. 1-16.

Figure 21:
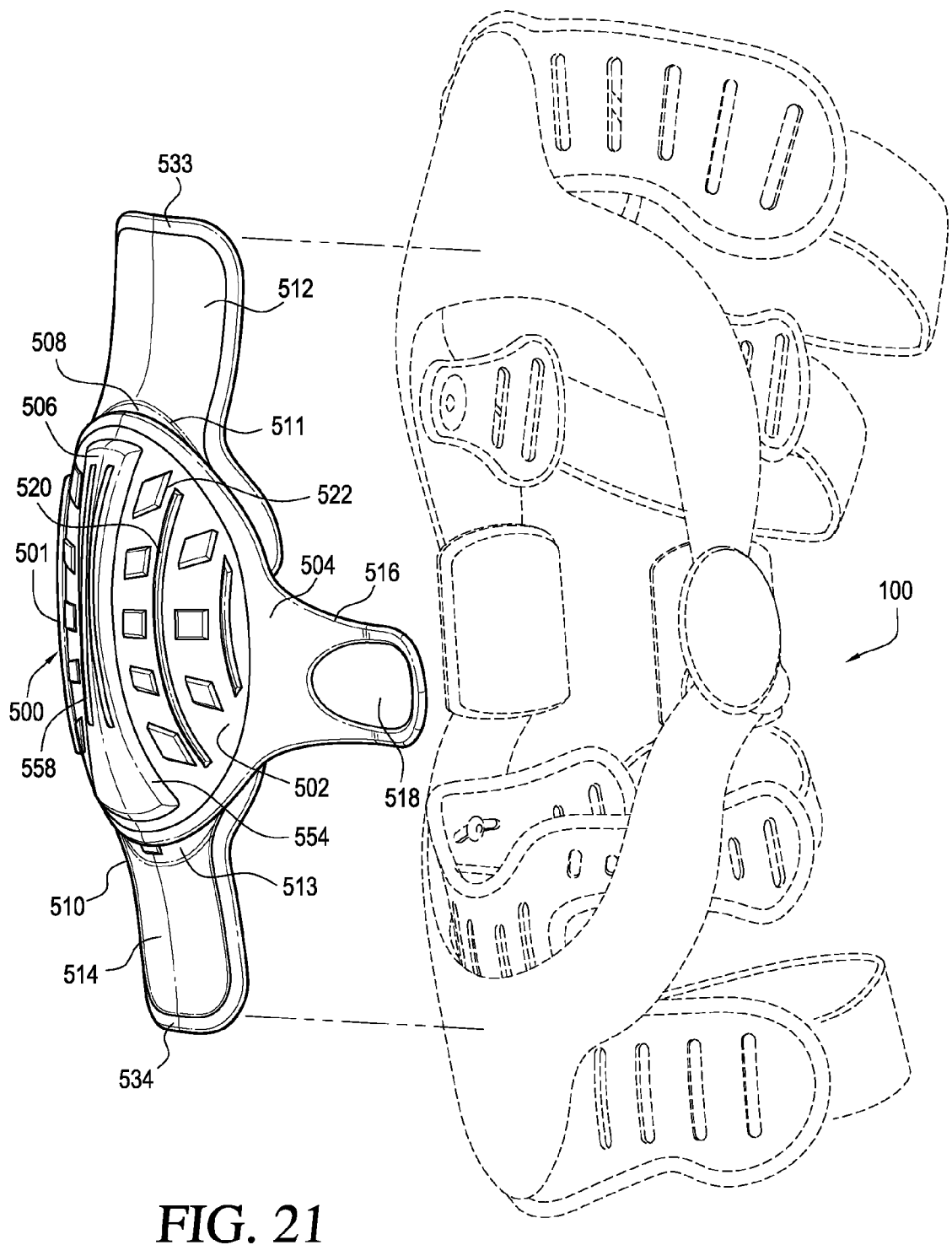
FIG. 21 is a front elevational view of a patella protector assembly in an extended configuration for use on the brace of FIG. 6.
Figure 22:
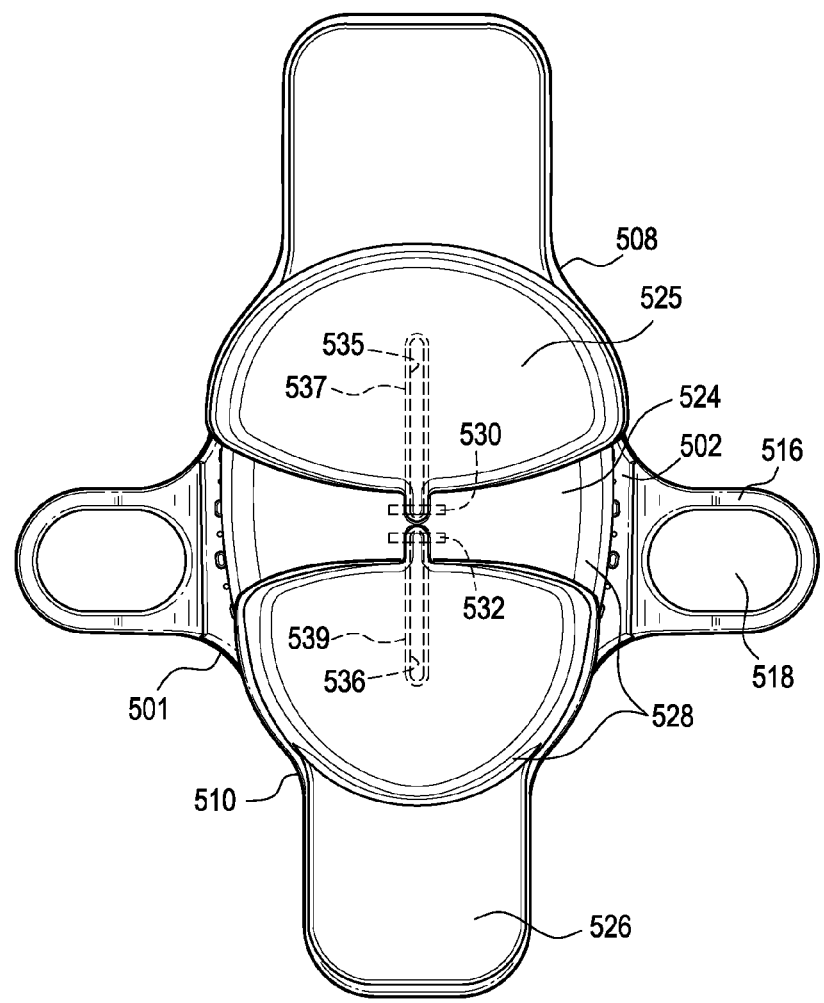
FIG. 22 is a rear elevational view of the patella protector assembly in FIG. 21.
Figure 23:
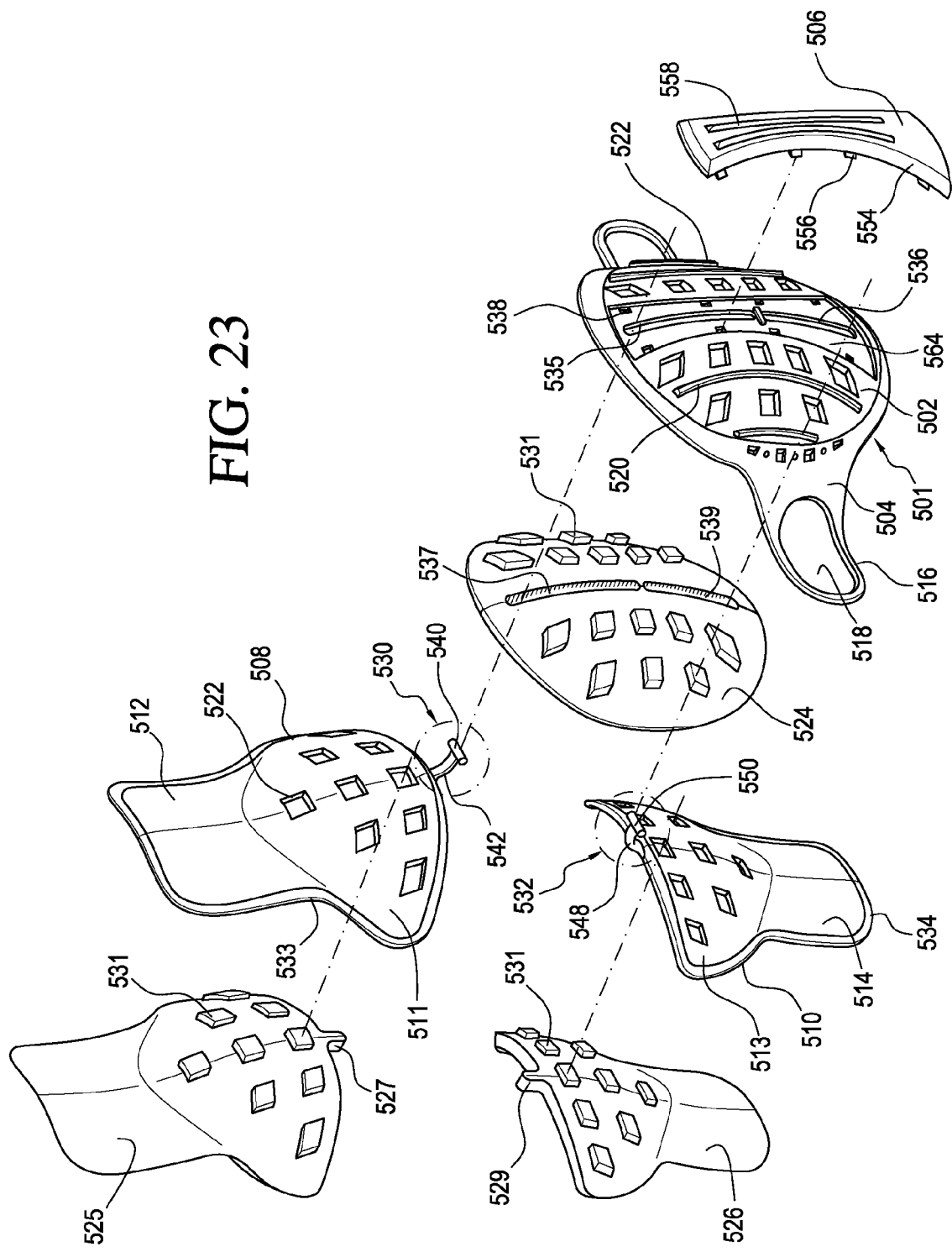
FIG. 23 is an exploded assembly perspective view of the patella protector assembly of FIG. 21.

In observing FIGS. 21-23, the orthopedic brace of FIG. 6 is shown including an orthopedic component in the form of a patella protector assembly 500. This assembly 500 includes an upper shell 508 and a lower shell 510 which are slidably and telescopically connected to a central shell 501 so as to cover the patella of a wearer and to leave no gap between any of the three shells 501, 508, 510. The central shell 501 is connected at the hinge of the brace, whereas the upper and lower shells 508, 510 are connected via extension portions 512, 514 or elastic elements (not shown), respectively, to upper and lower frame elements of the brace. Thus, as the leg moves, the central shell 501 moves relative to the upper and lower shells 508, 510 so as to accommodate flexion of the leg as the central shell 501 generally remains in place over the knee and hence the patella.

Figure 25:
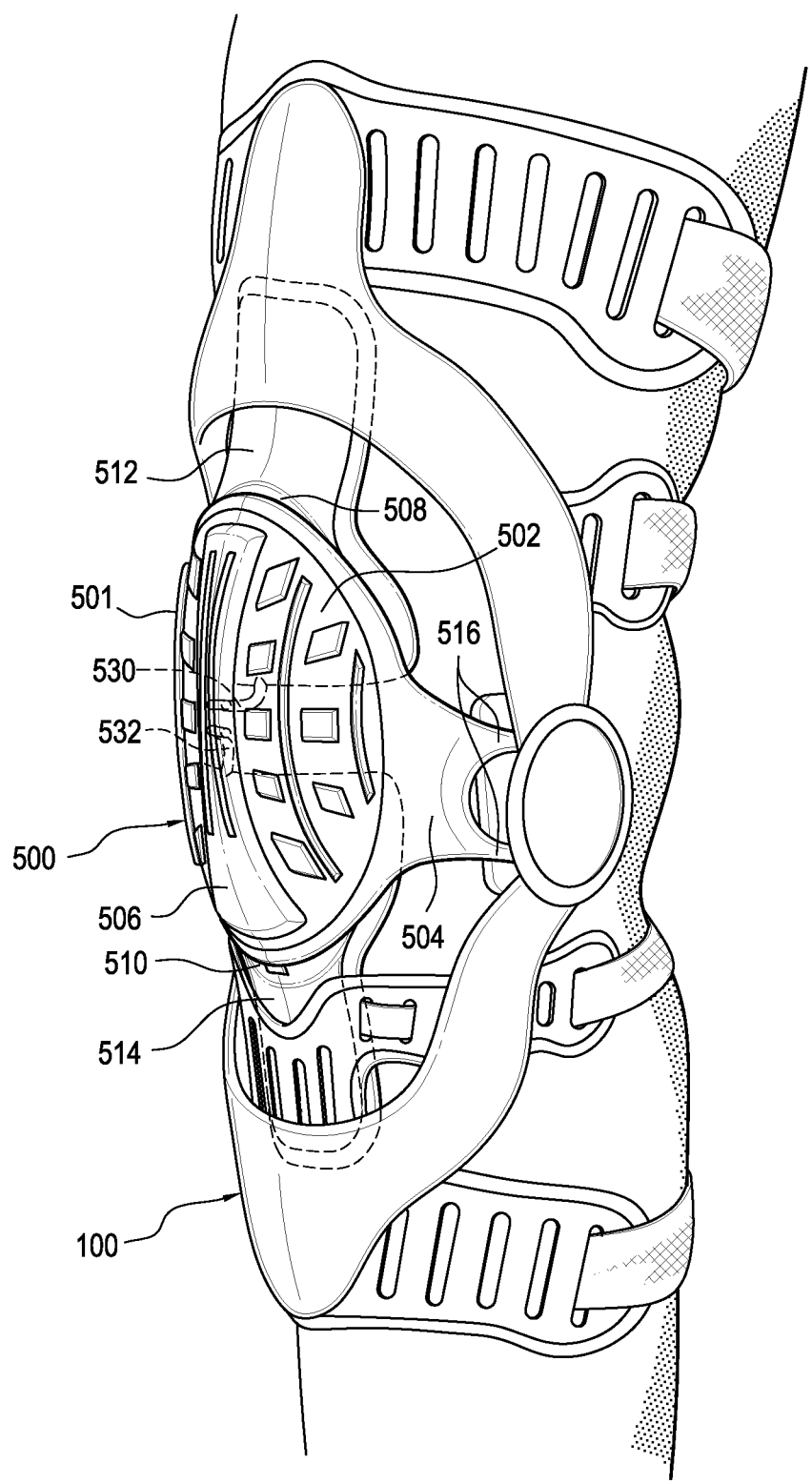
FIG. 25 is a schematic view of the patella protector assembly of FIG. 21 on the brace of FIG. 6 when a leg is in extension.
Figure 26:
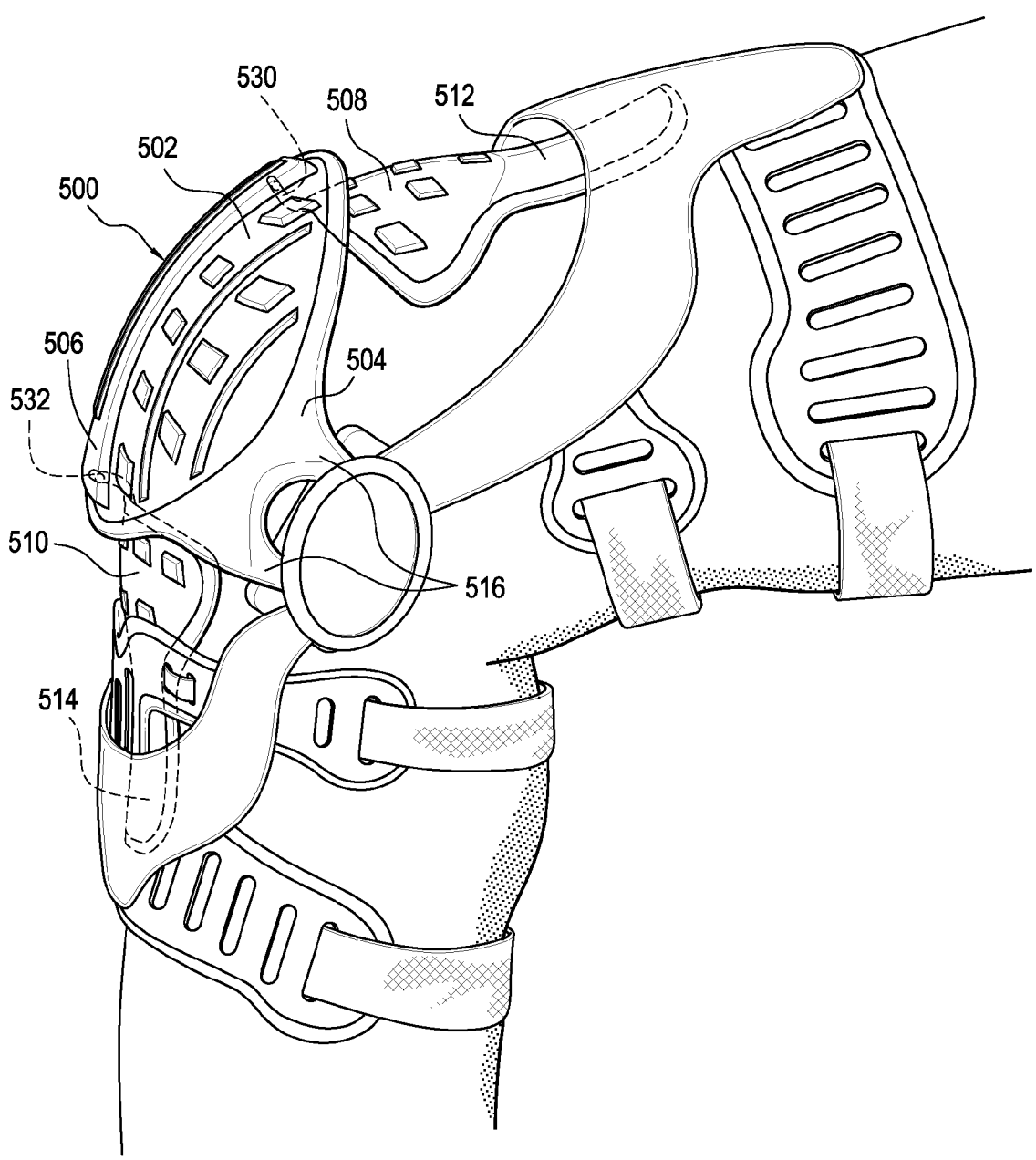
FIG. 26 is a schematic view of the patella protector assembly of FIG. 21 on the brace of FIG. 6 when a leg is in flexion.

For example, as shown in FIG. 25, the wearer has a knee in an extended position wherein the upper shell 508 is partially concealed under the central shell 501, and the lower shell 510 is likewise partially concealed under the central shell 501. When the knee is in flexion, as shown in FIG. 26, the upper shell 508 slides away from the central shell 501, and the lower shell likewise slides away from the central shell 501. In each position, and throughout the range of motion of the knee, the patella protector assembly provides protection of the patella and portions of the leg thereabout while accommodating movement of the knee and leg.

The connection of the upper and lower shells 508, 510 to the central shell 501 is generally concealed so as to minimize any parts extending from the patella protector assembly that may break or catch on anything. For example, the connection of the upper and lower shells 508, 510 to the brace frame elements is provided by way of the extension elements 512, 514 which are secured to an inner side of the frame assemblies of the brace by suitable fasteners such as rivets or hook and loop systems. These extension elements 512, 514 are generally contoured to accommodate the shape of corresponding section of the leg. The extension elements 512, 514 extend underneath or connect to the interior side of the frame assemblies of the brace so as to hide any fasteners. Likewise, as will be explained below, the connection of the upper and lower shells to the central shell is concealed so as to avoid exposing any connecting elements or fasteners that may be damaged from any impact during use of the patella protector assembly.

As depicted in FIGS. 22 and 23, the assembly 500 includes padding liners 524, 525, 526 which correspond to the shells 501, 508, 510, respectively. The liners are formed with contours 528 which accommodate the leg anatomy. The liners may be secured to the shells in accordance with known fasteners or adhesives, or alternatively the shells may be formed similarly to the embodiments of FIGS. 10-12 which include means to accommodate liners without the necessity of fasteners or adhesives. The shells and the liners hence are formed to closely follow the contours of the leg so as to maintain a streamlined and unobtrusive configuration which minimizes interference from apparel and equipment that may be used when the brace and assembly are worn together.

The liners may be constructed from open celled foam, such as EVA foam, so as to provide superior shock absorbing properties. The inner surface (surface adjacent the leg anatomy of the wearer) of the liner may include a layer material such as suede, nylon or other material selected for comfort and durability. The outer surface of the liner may include a layer of loop material and the inner surface of the shells may include suitable hook structure for engaging the loop material.

As illustrated in FIGS. 21 and 23, the central shell 501 includes a rigid main shell 502 and a more flexible perimeter edge portion 504 extending about the periphery of the main shell 502 is secured. This construction of the main shell 502 and the perimeter edge portion 504 is similar to that of the subshells in accordance with the embodiment of FIGS. 1-3 wherein the perimeter edge portion has greater flexibility than the top shell.

Unlike the aforementioned subshells in other embodiments described herein, the main shell is preferably more rigid and tougher than the subshells, and further the perimeter edge portion may likewise be formed from a tougher material that is resilient and not rigid like the main shell. For example, the main shell may be constructed from a blend of polyamide and ABS, such as the commercial product TERBLEND sold by BASF, so as to provide excellent impact strength, high surface quality, easy processing, chemical resistance, heat resistance and a pleasant feel. On the other hand, as with materials used in the aforementioned subshells, the perimeter edge portion may be constructed from thermoplastic polyurethane, such as ELASTOLLAN.

The perimeter edge portion 504 preferably extends about the entirety of the periphery of the main shell 502 so as to provide a compliant edge, and so as to secure to the brace via a resilient connection. The resilient connection is preferably defined by opposed wings 516 extending laterally relative to the central shell and are arranged for preferably securing about the hinge of the knee brace. Each wing 516 has an opening 518 configured for securing about a hinge, thereby permitting the insertion of the wing 516 between hinge plates of a hinge so as to clamp it to the brace. The opening 518 also may accommodate a condyle pad which may be secured to the hinge (as in pad 184 in FIG. 4).

Because the perimeter edge portion 504 is formed from a substantially resilient material, it can withstand twisting of the knee and still support the main body relative to the hinges. This is advantageous when the brace is used for sports in that the patella protector assembly can, while overall providing resistance and protection, accommodate minor movements or shifting of the knee while still covering the knee. This further provides comfort to the wearer in that the perimeter edge portion allows for a more comfortable fitting about the knee while the central shell still provides sufficient protection by way of the rigid top shell.

The upper and lower shells 510, 512 are constructed similarly to the central shell 501, in that each of the shells 510, 512, includes a main body 511, 513, the extensions 513, 514, respectively, and include a perimeter edge portion 533, 534, respectively. These shells can be formed from the same aforementioned materials used for forming the central shell.

The central shell 501 has an arcuate cross-section which is generally contoured to accommodate the patella portion of the anterior knee. The upper and lower shells 510, 512 are correspondingly contoured in cross-section to generally permit pivoting of at least 90° relative to and from one end connected to the central shell without interference by the central shell. Moreover, and quite advantageously, the contour of the upper and lower shells closely corresponds to the central shell so as to minimize gaps between the shells upon extension and flexion of the knee, and thus movement of the shells relative to one another.

This unique cooperation and configuration among the shells imparts superior articulation of the shells relative to one another. The cooperation and configuration allows the assembly to afford protection of knee while allowing for an ease of movement among the shells and comfort to the wearer without hindering performance of the wearer in movement of the knee. Advantageously, the concepts of the patella protector assembly may be extended to a variety of suitable other configurations to protect other anatomy other than a knee.

As with the aforementioned subshells, the central shell 501, and the upper and lower shells 510, 512 define a ventilation feature 522, formed by way of a plurality of apertures that are arranged in a predetermined pattern. The ventilation feature may be used in combination with the liners 524, 525, 526, of the type described above, thereby providing the same benefits of the aforementioned subshells. The liners may form nubs 531 which extend through the apertures of the ventilation feature 522.

The main shell 502 includes a plurality of elongate ribs 520 protruding outwardly from a front surface thereof. These ribs 520 may be formed from the same material as the main shell 502, or may be formed from a different material (having different toughness and impact resistance) and molded directly onto the top shell in areas thereof of increased thickness. These ribs 520 are advantageous in that they serve to reinforce the main body and deflect impact thereby assisting in the prevention of damaging of the top shell.

The central shell 501 forms elongate slots 535, 536 which extend in the longitudinal direction thereof. These elongate slots 535, 536 open to both the front and rear surfaces of the central shell 501, and are arranged to accommodate shell retention elements belonging to the upper and lower shells, as will be discussed below. The slots 535, 536 also correspond to slots 537, 539 formed in the liner 524, as depicted in FIG. 23. Along the front surface, the central shell 501 forms an elongate recess 564 into which the slots 535, 536 open into.

The elongate recess 564 is arranged to accommodate a buttress 506 that protrudes outwardly from the front surface of the main shell 502 and generally spans the longitudinal length of the main shell 502. The buttress 506 is preferably formed from a material that is tougher than the main shell 502 so as to provide improved impact resistance at the center of the patella protector assembly. Since the material used to form the buttress may have a greater weight, the size and location of the buttress may be limited so as to allow for lighter weight materials to be used for the main body thereby providing a lightweight patella protector assembly.

Figure 24:
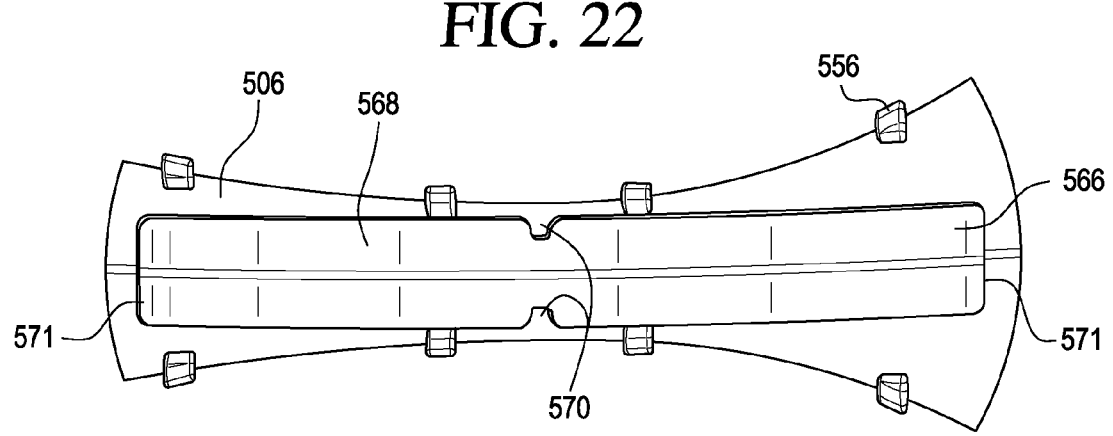
FIG. 24 is a rear elevational view of a buttress depicted in FIG. 23.

As illustrated in FIG. 24, the buttress 506 defines a plurality of nubs 556 which engage notches 538 formed along the recess 564 of the main shell 502. This allows for the buttress 506 to be separately formed from the main shell 502 and inserted into the recess 564. In the alternative, the buttress 506 may be directly molded or inserted into the central shell 501 whereby by the nubs 556 interlock with the notches 528. The buttress 506 also defines a plurality of ribs 558 serving a similar function to the ribs 520 formed on the central shell 501. Further, while the buttress 506 extends outwardly from the front surface of the top shell, the peripheral edges 554 of the buttress 506 are preferably beveled so as to minimize sharp edges and provide greater impact resistance.

Each of the upper and lower shells 508, 510, has a shell retention element 530, 532. Each shell retention element 530, 532 defines a generally arcuate neck 542, 548 formed along an end portion proximate to the central shell. A cross-bar 540, 550 is formed from each of the necks 542, 548, respectively.

The cross-bars 540, 550 are formed so as to slidably engage the front surface area around the slots 535, 536 of the central shell 501. Thus, the cross-bars 540, 550 have a width greater than the slots 535, 536. The necks 542, 548 thus have a height that is minimally greater than the combined thickness of the central shell 501 and the liner 524 since the necks 542, 548 effectively are located within the slots 535, 536, 537, 539 so as to permit the cross-bars 540, 550 to engage and slide relative to the slots 535, 536 and extend into the recess 564.

FIG. 24 shows the back surface of the buttress 506 wherein opposed recesses 566, 568 are defined and have a width greater than a width of the cross-bars 540, 550. Limits 570 are likewise formed to prevent sliding of the cross-bars 540, 550 in a first direction (extension of the assembly), and limits 571 prevent sliding of the cross-bars 540, 550 in second direction (flexion of the assembly). The recesses 566, 568 effectively combine with the recess 564 to control sliding of the cross-bars 540, 550.

From the shape of the neck and cross-bars of each shell retention element, the upper and lower shells are able to pivotably articulate, via particularly the shape of the arcuate neck, to accommodate movement of the knee as such shells slide relative to one another as the knee goes between extension and flexion. In other words, the upper and lower shells are able to rotate at the shell retention elements relative to the central shell. Thus, not only do the shells slide relative to one another, rotational movement is permitted which allows the wearer of the assembly to articulate the knee without hindrance while affording the necessary protection.

It will be pointed out that certain features of the assembly may be replaced by elastic elements. For example, the shell extensions may be replaced by or connect to the frame assemblies of a brace via elastic elements. Alternatively, the shell retention elements may be replaced with elastic elements which connect the upper and lower shells to the central shell.

While the foregoing embodiments have been described and shown, it is understood that alternatives and modifications of these embodiments, such as those suggested by others, may be made to fall within the scope of the invention.

The invention claimed is:

1. An orthopedic device, comprising:
   a rigid frame defining lateral and medial sides, the frame including a plurality of structural elements, the plurality of structural elements including proximal and distal frame assemblies connected to one another by at least one hinge, at least one of the proximal and distal frame assemblies having a central support and a central stem protruding from the central support;
   at least one strap connecting to the lateral and medial sides of the frame; and
   a flexible subshell connected to and extending flexibly and laterally outwardly from the central support, the subshell depending freely from the frame outside of the central support, the subshell defining at least one aperture through which extends at least one fastener to mechanically secure the subshell to the frame by engaging the central support;
   a ventilated padding corresponding in shape to the at least one subshell;
   wherein the subshell defines a plurality of elongate slots arranged at predetermined locations, the slots corresponding to the ventilated padding to allow a passage of air through both the subshell and the padding.

2. The orthopedic device according to claim 1, wherein the subshell defines at least one strap slot, the first end of the at least one strap looped about the at least one slot for connecting the first end thereof with the subshell.

3. The orthopedic device according to claim 2, wherein the subshell includes a slot edge portion extending about at least a portion of the at least one strap slot, the slot edge portion having a greater hardness than the main body, thereby serving as a reinforcement to reduce or prevent chafing of the at least one strap against the subshell.

4. The orthopedic device according to claim 1, wherein the subshell defines at least one strap slot, the subshell having at least one reinforcement element protruding outwardly from the subshell and located about the at least one slot.

5. The orthopedic device according to claim 1, the subshell having at least one enlarged end portion sized greater than and flaring from a mid-span portion of the subshell.

6. The orthopedic device of claim 1, wherein the subshell is secured to the frame only by the at least one fastener.

7. An orthopedic device, comprising:
   a rigid frame;
   a flexible subshell connected to and extending flexibly outwardly from the rigid frame, the subshell defining first and second side portions extending from a central portion, the subshell defining at least one opening defined by the first side portion and overlapping a portion of the rigid frame;
   an elongate strap having at least one end directly connected to at least the first side portion, the strap urging the second end portion to bend relative to the rigid frame;
   a first tightenable fastener adjustably secured to the rigid frame and extending through the at least one opening, wherein the first side portion of the subshell is adjustable in location relative to the rigid frame;
   wherein the at least one opening is defined by a series of at least two slots located incrementally away from a periphery of the rigid frame;
   wherein the subshell defines at least one aperture at the central portion thereof through which extends at least one second tightenable fastener to mechanically and removably secure the subshell to the frame by engaging the frame.

8. The orthopedic device according to claim 7, wherein a portion of the first side portion extends beyond the rigid frame and the first fastener, and defines at least one elongate slot for receiving the strap.

9. A knee brace, comprising:
   a rigid frame defining lateral and medial sides and a central portion, the frame including a plurality of structural elements, the plurality of structural elements including proximal and distal frame assemblies connected to one another by at least one hinge;
   at least one strap connecting to the lateral and medial sides of the frame; and
   a flexible subshell connected to and extends laterally outwardly from the frame to at least one of lateral or medial sides of the knee brace, the subshell depending freely from the frame, the subshell defining at least one aperture through which extends at least one fastener to mechanically secure the subshell to the frame by engaging the frame;
   a ventilated padding corresponding in shape to the at least one subshell;
   wherein the subshell defines a plurality of elongate slots arranged at predetermined locations, the slots corresponding to the ventilated padding to allow a passage of air through both the subshell and the padding, the first end of the at least one strap looped about a first one of the plurality of elongate slots for connecting the first end thereof with the subshell.

10. The knee brace according to claim 9, wherein the subshell includes a slot edge portion extending about at least a portion of the first one of the plurality of elongate slots, the slot edge portion having a greater hardness than the main body, thereby serving as a reinforcement to reduce or prevent chafing of the first one of the plurality of elongate slots against the subshell.

11. The knee brace according to claim 9, wherein the subshell has at least one reinforcement element protruding outwardly from the subshell and located about the first one of the plurality of elongate slots.

12. The knee brace according to claim 9, wherein the subshell has at least one enlarged end portion sized greater than and flaring from a mid-span portion of the subshell.

13. The knee brace of claim 9, wherein the subshell is secured to the frame only by the at least one fastener.

* * * * *